(12) United States Patent
Galili et al.

(10) Patent No.: US 12,262,972 B2
(45) Date of Patent: Apr. 1, 2025

(54) DRAPE ADAPTOR

(71) Applicant: XACT ROBOTICS LTD., Caesarea (IL)

(72) Inventors: Ben Galili, Atlit (IL); Ofer Arnold, Ma'ale Tzviya (IL); Eran Zur, Karkur (IL)

(73) Assignee: XACT ROBOTICS LTD., Caesarea (IL)

( * ) Notice: Subject to any disclaimer, the term of this patent is extended or adjusted under 35 U.S.C. 154(b) by 912 days.

(21) Appl. No.: 16/621,557

(22) PCT Filed: Jun. 14, 2018

(86) PCT No.: PCT/IL2018/050658
§ 371 (c)(1),
(2) Date: Dec. 11, 2019

(87) PCT Pub. No.: WO2018/229773
PCT Pub. Date: Dec. 20, 2018

(65) Prior Publication Data
US 2020/0170740 A1    Jun. 4, 2020

Related U.S. Application Data

(60) Provisional application No. 62/603,928, filed on Jun. 16, 2017.

(51) Int. Cl.
*A61B 46/10*    (2016.01)
*A61B 1/00*    (2006.01)
(Continued)

(52) U.S. Cl.
CPC .......... *A61B 46/10* (2016.02); *A61B 1/00142* (2013.01); *A61B 34/30* (2016.02);
(Continued)

(58) Field of Classification Search
CPC ..... A61B 46/10; A61B 1/00142; A61B 34/30; A61B 34/70; A61B 46/23; A61B 46/40;
(Continued)

(56) References Cited

U.S. PATENT DOCUMENTS

| 5,640,977 A | 6/1997 | Leahy et al. |
| 6,716,215 B1 * | 4/2004 | David ................ A61B 17/1622 |
| | | 433/116 |

(Continued)

FOREIGN PATENT DOCUMENTS

| FR | 3041239 | 3/2017 |
| WO | 2011037394 | 3/2011 |

(Continued)

OTHER PUBLICATIONS

International Search Report, International Application No. PCT/IL2018/050658, dated Sep. 13, 2018.

(Continued)

*Primary Examiner* — Robert A Lynch
*Assistant Examiner* — Mikail A Mannan
(74) *Attorney, Agent, or Firm* — The Roy Gross Law Firm, LLC; Roy Gross

(57) ABSTRACT

A drape adaptor configured for coupling to a first component of a medical device and for receiving a medical tool. The first component of the medical device including a non-sterile portion of a driving mechanism. The drape adaptor comprises a sealing member configured for passing therethrough at least a portion of at least one component of a sterile portion of the driving mechanism. The drape adaptor is configured to enable transmission of torque from the first component of the medical device to the medical tool via direct engagement between the at least one component of the sterile portion of the driving mechanism and the non-sterile portion of the driving mechanism, through the sealing mem-
(Continued)

ber, without compromising the sterility of the environment external to the drape adaptor.

6 Claims, 22 Drawing Sheets

(51) Int. Cl.
    *A61B 17/00*     (2006.01)
    *A61B 34/00*     (2016.01)
    *A61B 34/30*     (2016.01)
    *A61B 46/00*     (2016.01)
    *A61B 46/20*     (2016.01)
    *A61B 46/23*     (2016.01)

(52) U.S. Cl.
    CPC .... *A61B 34/70* (2016.02); *A61B 2017/00477* (2013.01); *A61B 2046/205* (2016.02); *A61B 46/23* (2016.02); *A61B 46/40* (2016.02)

(58) Field of Classification Search
    CPC .... A61B 2017/00477; A61B 2046/205; A61B 34/74; A61B 46/00
    See application file for complete search history.

(56) References Cited

U.S. PATENT DOCUMENTS

| | | | |
|---|---|---|---|
| 7,008,373 B2 | 3/2006 | Stoianovici et al. | |
| 7,699,855 B2 | 4/2010 | Anderson et al. | |
| 7,886,743 B2 * | 2/2011 | Cooper | A61B 34/71 606/130 |
| 8,202,278 B2 | 6/2012 | Orban, III et al. | |
| 8,206,406 B2 | 6/2012 | Orban, III | |
| 8,348,861 B2 | 1/2013 | Glozman et al. | |
| 8,663,130 B2 | 3/2014 | Neubach et al. | |
| 9,326,825 B2 | 5/2016 | Cleary et al. | |
| 2006/0111723 A1 | 5/2006 | Chapolini et al. | |
| 2006/0229641 A1 | 10/2006 | Gupta et al. | |
| 2015/0202009 A1 | 7/2015 | Nussbaumer et al. | |
| 2016/0242861 A1 | 8/2016 | Flatt et al. | |
| 2016/0249990 A1 | 9/2016 | Glozman et al. | |
| 2016/0249991 A1 | 9/2016 | Glozman et al. | |
| 2017/0025848 A1 | 9/2017 | Galili et al. | |

FOREIGN PATENT DOCUMENTS

| | | |
|---|---|---|
| WO | 2016178028 | 11/2016 |
| WO | 2017179044 | 10/2017 |
| WO | 2017203531 | 11/2017 |
| WO | 2018055621 | 3/2018 |

OTHER PUBLICATIONS

Written Opinion of the International Searching Authority, International Application No. PCT/IL2018/050658, dated Sep. 13, 2018.

* cited by examiner

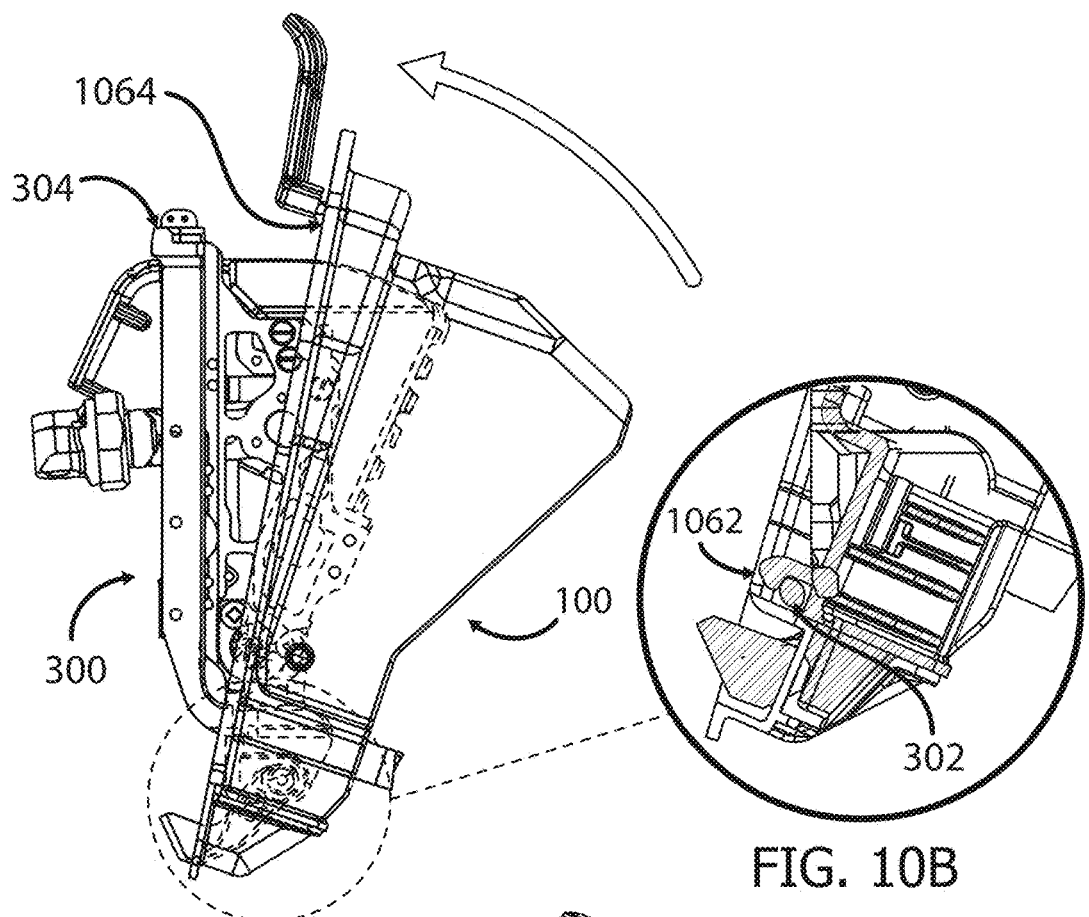
FIG. 10A
FIG. 10B
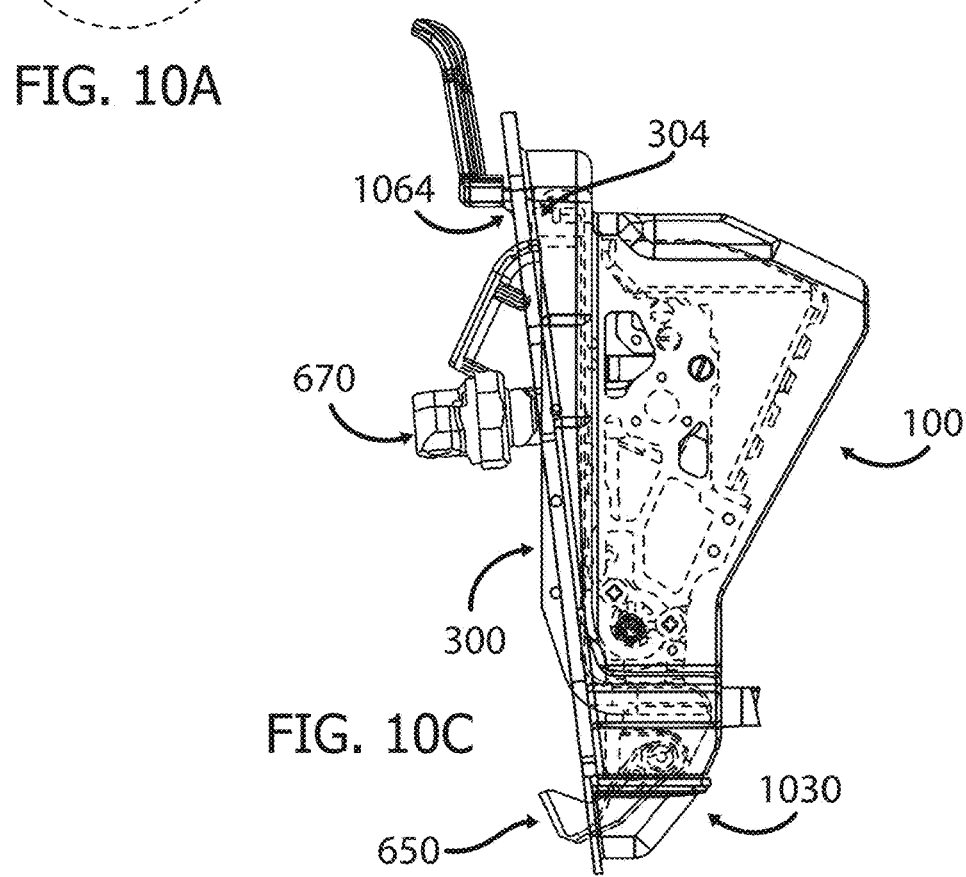
FIG. 10C

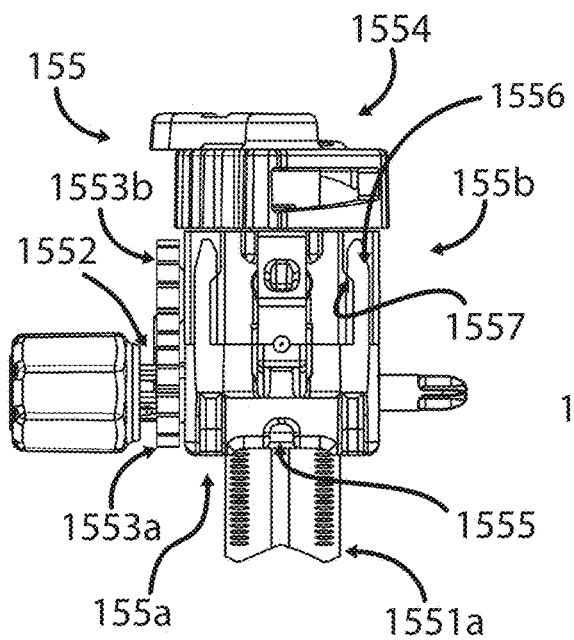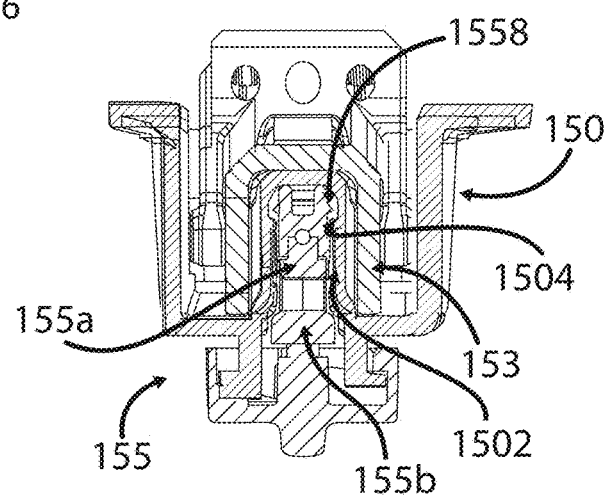
FIG. 15A  FIG. 15B
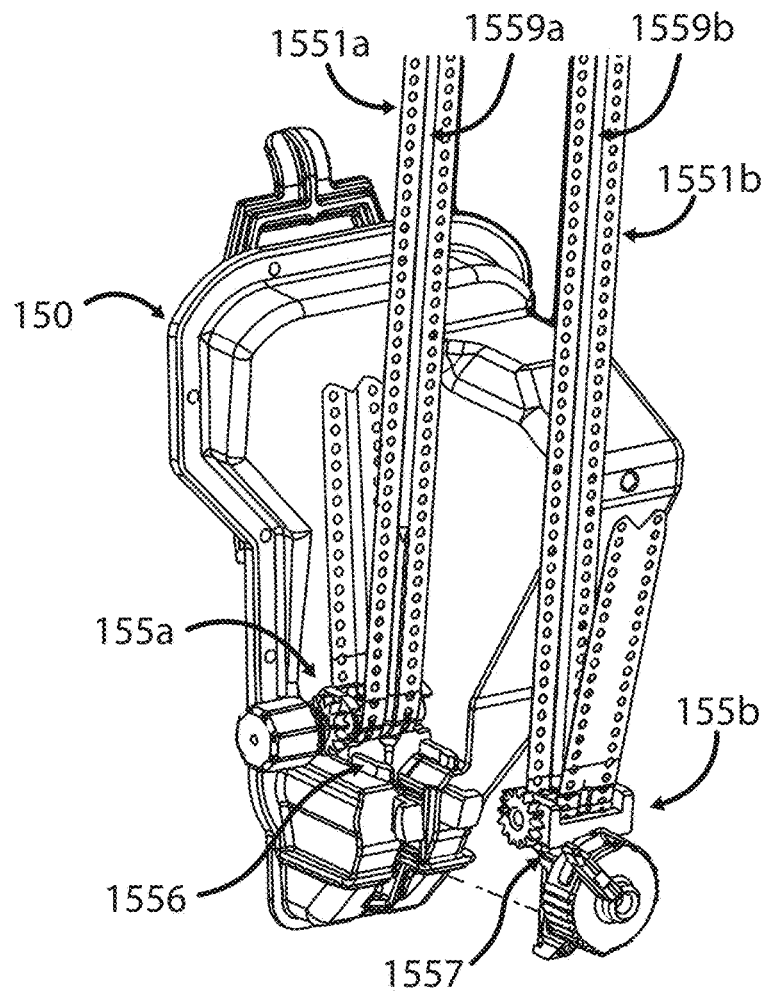
FIG. 15C

DRAPE ADAPTOR

RELATED APPLICATIONS

This application is a National Phase of PCT Patent Application No. PCT/IL2018/050658 having International filing date of Jun. 14, 2018, which claims the benefit of priority of U.S. Provisional Application No. 62/603,928 filed on Jun. 16, 2017 entitled DRAPE ADAPTOR. The contents of the above applications are all incorporated by reference as if fully set forth herein in their entirety.

FIELD OF THE INVENTION

The present invention relates to the field of sterile draping for medical devices, specifically to sterile draping for automated medical devices having both reusable and disposable parts, and more specifically to a drape adaptor that enables transfer of torque and/or force between the reusable and disposable parts.

BACKGROUND

Many routine treatments employed in modern clinical practice involve percutaneous insertion of medical tools, such as needles and catheters, for biopsy, drug delivery and other diagnostic and therapeutic procedures. The aim of an insertion procedure is to place the tip of an appropriate medical tool safely and accurately in a target region, which could be a lesion, tumor, organ or vessel. Examples of treatments requiring insertion of such medical tools include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

Guidance and steering of medical tools in soft tissue is a complicated task that requires good three-dimensional coordination, knowledge of the patient anatomy and a high level of experience. Therefore, image-guided automated (e.g., robotic) systems have been proposed for performing these functions. Among such systems are those described in U.S. Pat. No. 7,008,373 to Stoianovici, for "System and method for robot targeting under fluoroscopy", U.S. Pat. No. 8,348,861 to Glozman et al, for "Controlled Steering of a Flexible Needle", U.S. Pat. No. 8,663,130 to Neubach et al, for "Ultrasound Guided Robot for Flexible Needle Steering" and U.S. Patent Application Publication No. 2016/0249991 to Glozman et al, for "Gripper for Robotic Image Guided Needle Insertion", all of which are incorporated herein by reference in their entireties.

However, using automated devices for performing medical procedures introduced new challenges. One such challenge relates to the need to maintain a sterile environment in the procedure room and to the automated device being typically reusable, at least in part. During the procedure, the patient's blood and other bodily fluids and tissues may soil the device, and since the same automated device is to be used for performing a medical procedure on another patient, cross-contamination between patients may occur. If a non-sterile component comes in contact with the patient's body during the procedure, the patient may be infected with a variety of bacteria and other contaminants, which may be hazardous to his/her health. However, automated devices typically include electromechanical components, such as motors, sensors and electrical wires, which cannot undergo sterilization, therefore, these devices cannot undergo a sterilization process between consecutive procedures.

Further, some automated devices include both reusable and disposable parts. The disposable part may include a medical instrument/tool, such as a needle, which is coupleable to a reusable part of the device. In some cases, a portion of the driving mechanism, such as an insertion mechanism, may also be disposable. Separation between the reusable and disposable parts is required, and in the latter cases, such separation must also allow torque/force transfer between the reusable and disposable portions of the driving mechanism, without compromising the sterile environment.

Thus, use of sterile drapes to cover non-sterile medical devices, typically robotic surgical arms, has become common practice, as described, for example, in U.S. Pat. No. 7,699,855 to Anderson et at., U.S. Pat. No. 7,886,743 to Cooper et al, U.S. Pat. Nos. 8,202,278 and 8,206,406 both to Orban, III et al, and U.S. Patent Application No. 2015/0202009 to Nussbaumer et al.

In recent years, body-mounted automated devices have been introduced. Some of these devices are guiding devices that help in choosing the insertion point and in aligning the needle with the insertion point and with the target and the physician then inserts the needle manually, and some are steering devices that also insert the needle towards the target, as disclosed, for example, in U.S. Application Publication No. 2006/0229641 to Gupta et al, U.S. Pat. No. 9,326,825 to Cleary et al, U.S. Patent Application Publication No. 2016/0249990 to Glozman et al and International Patent Application Publication No. WO/2017/203531 to Arnold et al, all of which are incorporated herein by reference in their entireties.

In body-mounted devices, since the device is mounted on the patient's body, it is of utmost importance to ensure that the non-sterile parts of the device are maintained covered throughout the entire medical procedure, such that none of the non-sterile components of the device can contact the patient's body. Further, it is of utmost importance to ensure that covering the non-sterile parts of the device does not compromise the stability of the device and its positioning on the patient's body.

In some cases, the driving mechanism of the automated device includes both reusable and disposable parts, such that the interface between the reusable and disposable parts is direct, such as via engaging gears, as disclosed, for example, in co-owned U.S. Patent Application Publication No. 2017/0258489 to Galili et al, for "Insertion Guide", which is incorporated herein by reference in its entirety. Threading a drape sheet between engaging gears is likely to result in tearing of the drape sheet, which may not only compromise the sterile environment, but also jam the gears and disable the driving mechanism of the automated device.

Thus, there is a need for systems, devices and methods that overcome the deficiencies of the prior art.

The disclosures of each of the publications mentioned in this section and in other sections of the specification, are hereby incorporated by reference, each in its entirety.

SUMMARY

The present disclosure describes a sterile drape used to cover a medical device during a medical procedure performed in a sterile environment. The medical device may be reusable, at least in part, and/or it may include components, such as electronic components, which cannot undergo a sterilization process. In order to minimize the risk of infecting the patient with bacteria or other contaminants during the procedure, as well as the risk of cross-contamination between patients when non-sterile portions of the device are used in subsequent procedures, all non-sterile portions of the device must be sufficiently covered, such that there is no direct contact between the non-sterile and sterile portions of the device, as well as between the non-sterile portions of the device and the medical staff and the patient.

In some implementations, the sterile drape may include a drape sheet, which is configured to cover at least a portion of a medical device. The sterile drape may further include a drape adaptor, which is configured to be coupled to a reusable component of the device. The device may be automated (e.g., robotic), and the reusable component to which the drape adaptor is coupled may be a robotic end effector, for example. The drape adaptor may be further configured to receive a medical tool, such as a needle, introducer, etc. The medical tool may be part of a disposable unit of the medical device, which is coupleable to the drape adaptor. In some implementations, the disposable unit of the medical device and the drape adaptor are manufactured as an integral unit, such that the drape adaptor together with the disposable unit are coupled together to the reusable component of the device. The drape adaptor may be attached to the drape sheet using ultrasonic welding, heat welding or any other applicable attachment method.

The medical device may include a driving mechanism, such as an insertion mechanism for inserting a needle, or any other insertable medical tool, into the patient's body. In some implementations, the driving mechanism includes at least two separate portions, one positioned in the non-sterile portion of the device, and the other positioned in the sterile portion of the device. The sterile portion is typically coupled to the medical tool. In such implementations, in order for the driving mechanism to function, the non-sterile and sterile portions of the mechanism must engage with each other, without compromising the sterility of the sterile environment.

Thus, in some implementations, the drape adaptor may be configured to enable transmission of torque from a non-sterile portion of the driving mechanism to the sterile portion of the driving mechanism, or vice versa. The drape adaptor may include, for example, a sealing member, such as an O-ring or an overmold elastic material, which is positioned between the two portions of the driving mechanism, after coupling the drape adaptor to the reusable component of the medical device (e.g., end effector) and coupling the medical tool to the drape adaptor. The sealing member may be configured such that the sterile portion of the driving mechanism, or a component of the sterile portion, can be translated through the sealing member, either manually of automatically, and engage with the non-sterile portion of the driving mechanism, or with a component of the non-sterile portion, which is positioned on the other side of the sealing member. The sealing member may close around the sterile component, such that separation between the sterile and non-sterile portions of the driving mechanism is maintained.

In some implementations, the sterile and non-sterile engaging components may be a drive axis and a gear, respectively. The gear may be provided with, or coupled to, a cylinder, which is configured to rotate together with the gear. The cylinder may be substantially hollow, and it may be configured to receive a tip of the drive axis, such that rotation of the gear results in rotation of the drive axis, via rotation of the cylinder. In some implementations, the cylinder may include inner ridges/teeth, and the tip of the drive axis may include corresponding outer ridges/teeth, such that as the drive axis is being received within the cylinder, the outer ridges of the drive axis' tip engage with the inner ridges of the cylinder. The gear and the cylinder may be manufactured as a single part or they may be manufactured as two separate parts assembled together. In some implementations, the gear may be a bevel gear. The gear together with the cylinder may be referred to as "female gear" or "female bevel gear".

In some implementation, the drive axis is part of a disposable unit of the medical device, and it may be moveable between a retracted state and an extended state. In case the medical device is an insertion device, the disposable unit may be an insertion module. In some implementations, prior to coupling the disposable unit to the drape adaptor, the drive axis is in its retracted state, and once the disposable unit is coupled to the drape adaptor, the drive axis is moved to its extended state, either manually or automatically. In case the disposable unit and the drape adaptor are an integral unit, the drive axis is moved to its extended state after the drape adaptor with the integral disposable unit are coupled to the reusable unit of the device. As the drive axis is being moved to its extended state, it passes through the sealing member of the drape adaptor and then engages with the gear's cylinder.

In some implementations, after the disposable unit (e.g., insertion module) is received within its dedicated space within the drape adaptor, it should be pushed further into its dedicated space to be properly and securely positioned within the adaptor. In case the sterile portion of the driving mechanism comprises a drive axis and the non-sterile portion of the driving mechanism comprises a female gear, proper alignment between the drive axis and the female gear, i.e., to ensure engagement between the tip of the drive axis and the cylinder upon moving the drive axis from its retracted state to its extended state, may be achieved only upon performing a tightening action of the disposable unit against the adaptor. Thus, in some implementations, the disposable unit may include a tightening knob and capturing elements which engage with tightening members of the adaptor, upon rotating or pressing the tightening knob, for example. In some implementations, the disposable unit's capturing elements comprise at least one slot in the tightening knob, which has at least one inclined surface, and the adaptor's capturing members comprise at least one hook, which engages with the slot, such that continued rotation of the tightening knob causes the hook to push the inclined surface and thus the tightening knob and the entire disposable unit to which the knob is rigidly coupled, inwardly, until the disposable unit reaches its final position within the adaptor, and the tightening knob cannot be rotated any further in the same direction. In other implementations, the capturing elements of the tightening knob may be configured as one or more external flags, which engage with the adaptor's hooks.

In some implementations, the drape adaptor may comprise a substantially rigid portion, which is configured to cover at least one non-sterile component of the medical device, such as the end effector, and a substantially elastic/flexible portion, which is configured to cover another non-sterile component of the device, such as a gimbal to which the end effector is coupled, for example, at its distal end. In some implementations, the medical device is configured for attachment to the patient's body, and thus covering the bottom/distal gimbal with a more flexible material is to allow free movement of the gimbal while limiting the size of the bottom section of the drape adaptor, so as to minimize contact of the drape adaptor with the patient's skin.

The drape adaptor may further include a frame, which may also be manufactured from a substantially elastic material. The frame may surround the entire adaptor, so as to provide a uniform surface for attaching the adaptor to the drape sheet using heat or ultrasonic welding, for example.

In some implementations, the drape adaptor may include one or more rear connectors, which are configured to couple the drape adaptor to the abovementioned reusable component of said medical device, e.g., the end effector. The rear connectors may be in the form of latches, which establish a snap-fit connection with corresponding connectors in the end effector. The adaptor may further include one or more positioning members, which are configured to ensure correct placement of the adaptor on the end effector, as well as its stability once coupled.

In some implementations, the drape adaptor may further include one or more front connectors, which are configured to couple the disposable unit, which includes, inter alia, the medical tool, to the drape adaptor. The connection between the disposable unit and the drape adaptor may also be a snap-fit connection. In some implementations, the disposable unit may be modular and comprise at least two parts, such as a rear part and a front part, to allow the clinician to disconnect the two parts of the disposable unit from each other and remove them from the medical tool (e.g., needle), leaving the tool inserted in the patient's body. In such implementations, only the rear part of the disposable unit is coupled to the drape adaptor, and the connection may be such that once it is established, the rear part can no longer be disconnected from the adaptor. It can be appreciated that the connection between the disposable unit's rear and front parts should be weaker than the connection between the rear part and the adaptor, so that disconnection of the front part from the rear part would not cause the entire disposable unit to disconnect from the adaptor.

In some implementations, the drape sheet may include one or more fasteners, which secure the drape sheet to the medical device, e.g., to the device's base, to ensure that the drape sheet is not unintentionally removed from the device, even partially, which may compromise the sterile environment, during the medical procedure. Such fasteners may comprise latches, semi-flexible protrusions, hooks and loops, or any other suitable fastener.

In some implementations, the medical device is configured to be attached on the patient's body, either directly or by means of a mediator plate/base. In such implementations, once the medical device is covered, it is placed in the desired position on the patient's body, and secured thereto, e.g., using one or more straps. The straps may be separate from the drape and coupled to anchors on the medical device using hooks, which are configured to be coupled to the anchors over the drape sheet, such that they do not rip the drape sheet. In other implementations, the straps are attached to the external (sterile) side of the drape sheet, while the hooks are attached to the inner (non-sterile) side of the drape sheet.

There is provided herein, according to some embodiments, a drape adaptor, having an adaptor body configured for coupling to a first component of a medical device and for receiving an insertable medical tool, the first component including a non-sterile portion of a driving mechanism; and a sealing member coupled to the adaptor body and configured for passing therethrough at least a portion of at least one component of a sterile portion of the driving mechanism; wherein the drape adaptor is configured to enable transmission of torque from the first component of the medical device to the insertable medical tool via direct engagement between at least one component of the sterile portion of the driving mechanism and the non-sterile portion of the driving mechanism, through the sealing member, without compromising the sterility of the environment external to the drape adaptor.

According to some embodiments, the non-sterile portion of the driving mechanism includes a gear and at least one component of the sterile portion of the driving mechanism may include a drive axis. In some embodiments, the gear may be coupled to a hollow cylinder configured to rotate together with the gear, and wherein the hollow cylinder is further configured to receive a tip of the drive axis, such that rotation of the gear results in rotation of the drive axis. The hollow cylinder may include inner grooves configured to receive corresponding outer ridges of the tip of the drive axis. In some embodiments, the drive axis is moveable between a retracted state and an extended state, wherein moving the drive axis from the retracted state to the extended state causes the drive axis to pass through the sealing member and be received within the hollow cylinder.

The adaptor body may include a substantially rigid portion configured for covering at least a portion of the first component of the medical device and a substantially elastic portion configured for covering at least a portion of a second component of the medical device. The first component of the medical device may be a robotic end effector. The second component of the medical device may be a gimbal to which the robotic end effector is coupled. The medical device may include a disposable unit. In some embodiments, the disposable unit includes the insertable medical tool and the sterile portion of the driving mechanism. The medical device may include a reusable unit. The reusable unit may include the first component of the medical device. The adaptor body may include a projecting section configured for covering at least a portion of the non-sterile portion of the driving mechanism. The adaptor body may include an opening, and wherein the sealing member is disposed within the opening. The drape adaptor may include a frame coupled to the adaptor body. In some embodiments, the frame being configured for attaching to a drape sheet configured to cover at least a portion of the medical device, which may include a mechanism for steering the insertable medical tool. In some embodiments, the drape adaptor includes one or more rear connectors configured to couple the adaptor body to the first component of the medical device. In some embodiments, the drape adaptor includes one or more release handles coupled to one or more rear connectors, and configured to release the adaptor body from the first component of the medical device. In some embodiments, the adaptor body includes at least one protrusion configured to facilitate aligning the adaptor body with the first component of the medical device. In some embodiments, the adaptor body includes one or more front connectors configured to couple the disposable unit to the adaptor body. In some embodiments, the disposable unit includes at least two detachable parts, and wherein one or more front connectors are configured to engage with corresponding one or more connectors positioned on a first of at least two parts, such that upon detaching a second of at least two detachable parts from the first of at least two detachable parts, the first of at least two detachable parts remains coupled to the adaptor body. In some embodiments, the disposable unit includes a tightener configured to tighten the disposable unit against the adaptor body. The tightener may include a tightening knob. In some embodiments, the driving mechanism is a mechanism for inserting the insertable medical tool into a body of a subject. In some embodiments, the disposable unit of the medical device and the drape adaptor are a single integral unit. In some embodiments, the medical device is configured to be mounted on a body of a subject. The drape adaptor may be foldable. The insertable medical tool may include one or more of: a needle, an introducer, a catheter, a cannula, a port, an electrode rod, a surgical tool and a fluid delivery tool.

According to an aspect of some embodiments of the present disclosure, there is provided a drape adaptor, having: an adaptor body configured for coupling to at least a first component of a medical device and for receiving an insertable medical tool, at least a first component including a non-sterile portion of a driving mechanism; and a sealing member configured for passing therethrough at least one component of a sterile portion of the driving mechanism. In some embodiments, at least one component of the sterile portion of the driving mechanism is configured to engage with the non-sterile portion of the driving mechanism, positioned on the opposite side of the sealing member. In some embodiments, the adaptor body includes a substantially rigid portion configured for covering at least a portion of the first component of the medical device and a substantially elastic portion configured for covering at least a portion of a second component of the medical device. The first component of the medical device may be a robotic end effector. In some embodiments, the second component of the medical device is a gimbal to which the robotic end effector is coupled.

According to some embodiments of the present disclosure, there is provided a drape adaptor having a substantially rigid body portion configured for covering at least a first component of a medical device and a substantially elastic body portion configured for covering at least a second component of the medical device. In some embodiments, the substantially rigid body portion includes a projecting section configured for covering a non-sterile portion of a driving mechanism of the first component of the medical device and one or more rear connectors configured to couple the drape adaptor to the first component of the medical device. In some embodiments, the drape adaptor is configured to enable transmission of torque from the non-sterile portion of the driving mechanism to a sterile portion of a driving mechanism, while maintaining the sterility of the environment external to the drape adaptor. In some embodiments, the drape adaptor includes a sealing member coupled to the substantially rigid body portion, wherein the non-sterile portion of the driving mechanism and the sterile portion of the sterile portion of the driving mechanism are initially positioned on opposite sides of the sealing member. The substantially rigid body portion may include an opening. In some embodiments, the sealing member is disposed within the opening. In some embodiments, the drape adaptor includes a frame coupled to at least one of the substantially rigid body portion and the substantially elastic body portion, the frame being configured for attaching to a sterile drape sheet. In some embodiments, the substantially rigid body portion includes one or more release handles coupled to one or more rear connectors, and configured to release the drape adaptor from the first component of the medical device. In some embodiments, at least one component of the sterile portion of the driving mechanism is configured to be translated through the sealing member, either manually or automatically, and engage with at least one corresponding component of the non-sterile portion of the driving mechanism. In other embodiments, at least one component of the sterile portion of the driving mechanism includes a drive axis having a tip. In some embodiments, at least one corresponding component of the non-sterile portion of the driving mechanism includes a hollow cylinder coupled to a gear, the hollow cylinder being configured to receive the tip of the drive axis. In some embodiments, the hollow cylinder includes inner ridges configured to engage with corresponding outer ridges of the tip of the drive axis. In some embodiments, the drive axis is moveable between a retracted state and an extended state, wherein moving the drive axis from the retracted state to the extended state causes the drive axis to be translated through the sealing member and the tip of the drive axis to be received within the hollow cylinder.

According to some embodiments, at least one of the a substantially rigid body portion and the a substantially elastic body portion further includes one or more front connectors configured to couple a disposable unit of the medical device to the drape adaptor, the disposable unit including a medical tool and the sterile portion of the driving mechanism.

According to some embodiments of the present disclosure, there is provided a sterile drape having a drape sheet configured for covering at least a portion of a medical device and a drape adaptor configured for attaching to the drape sheet. In some embodiments, the drape adaptor includes an adaptor body configured for coupling to a first component of the medical device and for receiving a medical tool, at least a first component including a non-sterile portion of a driving mechanism, and a sealing member coupled to the adaptor body and configured for passing therethrough at least a portion of at least one component of a sterile portion of the driving mechanism.

In some embodiments, the drape adaptor is configured to enable transmission of torque from the first component of the medical device to the medical tool via direct engagement between the sterile portion of the driving mechanism of the medical device and the non-sterile portion of the driving mechanism, without compromising the sterility of the environment external to the sterile drape. The adaptor body may include a projecting section configured for covering at least a portion of the non-sterile portion of the driving mechanism. In some embodiments, the adaptor body includes an opening, and wherein the sealing member is disposed within the opening. The drape adaptor may include a frame coupled to the adaptor body. In some embodiments, the frame being configured for attaching the drape adaptor to the drape sheet. In some embodiments, the sterile portion of the driving mechanism includes a drive axis moveable between a retracted state and an extended state. The non-sterile portion of the driving mechanism may include a gear and a hollow cylinder coupled to the gear and configured to receive a tip of the drive axis, such that rotation of the gear results in rotation of the drive axis. In some embodiments, moving the drive axis from the retracted state to the extended state causes the drive axis to pass through the sealing member and the tip of the drive axis to be inserted into the hollow cylinder. In some embodiments, the adaptor body includes a substantially rigid portion configured to cover at least a portion of the first component of the medical device and a substantially elastic portion configured to cover at least a portion of a second component of the medical device. The first component of the medical device may include a robotic end effector and the second component of the medical device may be a gimbal to which the robotic end effector is coupled. The medical device may include a disposable unit. In some embodiments, the disposable unit includes the medical tool and the sterile portion of the driving mechanism. The medical device may include a reusable unit. In some embodiments, the reusable unit including the first component of the medical device.

In some embodiments, the drape adaptor includes one or more rear connectors configured to couple the adaptor body to the first component of the medical device. In some embodiments, the drape adaptor includes one or more release handles coupled to one or more rear connectors, and configured to release the adaptor body from the first component of the medical device. The adaptor body may include at least one protrusion configured to facilitate aligning the adaptor body with the first component of the medical device. The drape adaptor may include one or more front connectors configured to couple the disposable unit to the adaptor body. In some embodiments, the disposable unit includes at least two detachable parts, and wherein one or more front connectors are configured to engage with corresponding one or more connectors positioned on a first of at least two parts, such that upon detaching a second of at least two detachable parts from the first of at least two detachable parts, the first of at least two detachable parts remains coupled to the adaptor body. The disposable unit may include a tightener configured to tighten the disposable unit against the adaptor body. The drape sheet may include one or more fasteners configured to secure the drape sheet to the medical device. The drape sheet may include one or more cushions attached to its bottom surface. In some embodiments, the driving mechanism is a mechanism for inserting the medical tool into a body of a subject. The disposable unit of the medical device may include an insertion module. In some embodiments, the disposable unit of the medical device and the drape adaptor are a single integral unit. In some embodiments, the medical device is configured to be mounted on a body of a subject. In some embodiments, the sterile drape includes one or more hooks attached to an internal surface of the drape sheet and one or more straps attached to an external surface of the drape sheet, wherein one or more hooks are configured to be coupled to one or more anchors on the medical device, and one or more straps are configured to secure the medical device to the body of the subject. The drape adaptor may be foldable. The medical tool may include one or more of: a needle, an introducer, a catheter, a cannula, a port, an electrode rod, a surgical tool and a fluid delivery tool.

According to some embodiments of the present disclosure, there is provided a sterile drape having a drape sheet configured for covering at least a portion of a medical device and a drape adaptor attached to the drape sheet. In some embodiments, the drape adaptor includes a substantially rigid portion configured for covering at least a first component of the medical device and a substantially elastic portion configured for covering at least a second component of the medical device. In some embodiments, the substantially rigid portion includes one or more rear connectors configured for coupling the drape adaptor to the first component of the medical device and one or more release handles coupled to one or more rear connectors, and configured for releasing the drape adaptor from the first component of the medical device.

In some embodiments, the first component of the medical device includes a robotic end effector, and the second component of the medical device includes a gimbal to which the robotic end effector is coupled. In some embodiments, the first component of the medical device includes a non-sterile portion of a driving mechanism. In some embodiments, the drape adaptor further includes a sealing member configured for passing therethrough at least one component of a sterile portion of the driving mechanism. In some embodiments, the drape adaptor is configured to enable direct engagement between the non-sterile portion of the driving mechanism and at least one component of the sterile portion of the driving mechanism, via the sealing member, without compromising the sterility of the environment external to the drape adaptor.

According to some embodiments of the present disclosure, there is provided a medical kit including a disposable unit having a medical tool and a second portion of a driving mechanism configured to transmit torque to the medical tool from a first portion of the driving mechanism positioned in a reusable unit of a medical device and a sterile drape. In some embodiments, the sterile drape includes a drape sheet configured to cover the reusable unit, and a drape adaptor configured to be coupled to the reusable unit and to receive the disposable unit. In some embodiments, the drape adaptor includes a sealing member. In some embodiments, the sealing member enables transmission of the torque without compromising the sterility of the environment external to the sterile drape.

In some embodiments, the second portion of the driving mechanism includes a sterile component configured to be translated, at least in part, through the sealing member, and to engage with a non-sterile component of the first portion of the driving mechanism positioned on the opposite side of the sealing member. In some embodiments, the drape adaptor includes a projecting section configured for covering at least a portion of the non-sterile portion of the driving mechanism. The drape adaptor may include a frame configured for attaching the drape adaptor to the drape sheet. The drape adaptor may include one or more rear connectors configured for coupling the drape adaptor to the reusable unit of the medical device. The drape adaptor may include one or more release handles coupled to one or more rear connectors, and configured to release the drape adaptor from the reusable unit. The drape adaptor may include at least one protrusion configured to facilitate alignment of the drape adaptor with the reusable unit. The drape adaptor may include one or more front connectors configured to couple the disposable unit to the drape adaptor.

In some embodiments, the disposable unit includes at least two detachable parts, and wherein one or more front connectors are configured to engage with corresponding one or more connectors positioned on a first of at least two parts, such that upon detaching a second of at least two detachable parts from the first of at least two detachable parts, the first of at least two detachable parts remains coupled to the drape adaptor. The disposable unit may include a tightener configured to tighten the disposable unit against the drape adaptor.

In some embodiments, the non-sterile component of the first portion of the driving mechanism includes a hollow cylinder coupled to a gear, and the sterile component of the second portion of the driving mechanism includes a drive axis. In some embodiments, the hollow cylinder is configured to receive a tip of the drive axis, and wherein the hollow cylinder is configured to rotate together with the gear, such that rotation of the gear results in rotation of the drive axis. The hollow cylinder may include inner grooves configured to receive corresponding outer ridges of the tip of the drive axis. In some embodiments, the drive axis is moveable between a retracted state and an extended state, and wherein moving the drive axis from the retracted state to the extended state causes the drive axis to pass through the sealing member and be received within the hollow cylinder.

In some embodiments, the medical tool is configured for insertion into a body of a subject. The medical tool may include one or more of: a needle, an introducer, a catheter, a cannula, a port, an electrode rod, a surgical tool and a fluid delivery tool. In some embodiments, the disposable unit includes a pair of flexible strips connected along at least part of their length and having a central channel therebetween adapted to receive and support the medical tool, and a pair of rollers disposed on either side of the pair of flexible strips and interacting therewith such that counter-rotation of the pair of rollers causes the pair of flexible strips and the medical tool to move between the pair of rollers. In some embodiments, the disposable unit further includes a holder configured to secure together a head member of the medical tool and the proximal end of the pair of flexible strips.

In some embodiments, the disposable unit and the drape adaptor are a single integral unit. In some embodiments, the medical device is configured to be mounted on the body of the subject.

According to some embodiments of the present disclosure, there is provided a method for covering a medical device with a sterile drape including a step of providing a sterile drape having a drape sheet configured for covering at least a portion of the medical device, and a drape adaptor attached to the drape sheet, the drape adaptor being configured for coupling to a first component of the medical device and for receiving a medical tool, wherein the drape adaptor is further configured to enable transmission of torque from the first component of the medical device to the medical tool via direct engagement between a non-sterile portion of a driving mechanism of the medical device and a sterile portion of the driving mechanism, without compromising the sterility of the environment external to the sterile drape. In some embodiments, the method for covering a medical device with a sterile drape includes a step of coupling the drape adaptor to the first component of the medical device. In some embodiments, the method for covering a medical device with a sterile drape includes a step of pulling the drape sheet over at least a portion of the medical device. In some embodiments, the method for covering a medical device with a sterile drape may include a step of securing the drape sheet to the medical device. In some embodiments, the method for covering a medical device with a sterile drape may include a step of coupling a disposable unit of the medical device, including the medical tool, to the drape adaptor.

According to some embodiments of the present disclosure, there is provided a method for enabling transmission of torque from a non-sterile component of a driving mechanism of a medical device to a sterile component of the driving mechanism, without compromising the sterile environment. In some embodiments, the method for enabling transmission of torque includes a step of providing a drape adaptor including an adaptor body and a sealing member coupled to the adaptor body. In some embodiments, the method for enabling transmission of torque includes a step of coupling the adaptor body to a first portion of the medical device, the first portion including the non-sterile component of the driving mechanism. In some embodiments, the method for enabling transmission of torque includes a step of translating at least a portion of the sterile component of the driving mechanism through the sealing member, until it engages with the non-sterile component of the driving mechanism positioned on the opposite side of the sealing member. In some embodiments, the method for enabling transmission of torque may include a step of coupling a disposable unit of the medical device to the drape adaptor, wherein the disposable unit includes the sterile component of the driving mechanism. In some embodiments, the drape adaptor is attached to a sterile drape sheet.

Implementations of the devices, systems and methods described above may further include any of the features described in the present disclosure, including any of the features described hereinabove in relation to other device, system and method implementations.

The terms "implementation" and "embodiment" are used interchangeably throughout this disclosure.

It is to be understood that the terms proximal and distal as used in this disclosure have their usual meaning in the clinical arts, namely that proximal refers to the end of a device or object closest to the person or machine inserting or using the device or object and remote from the patient, while distal refers to the end of a device or object closest to the patient and remote from the person or machine inserting or using the device or object.

It is also to be understood that although some examples used throughout this disclosure relate to a needle, this is done for simplicity reasons alone, and the scope of this disclosure is not meant to be limited to a needle, but is understood to include any medical tool which is insertable into the subject's body for diagnostic and/or therapeutic purposes, including an introducer, catheter, cannula, port, electrode rod, surgical tool, fluid delivery tool, or any other such insertable tool.

In addition, the terms "subject" and "patient" are used interchangeably throughout this disclosure and may refer to any human or animal undergoing the medical procedure.

Further, the terms "user", "physician", "clinician" and "medical staff" are used interchangeably throughout this disclosure and may refer to any person taking part in the performed medical procedure.

BRIEF DESCRIPTION OF THE DRAWINGS

Some exemplary implementations of the devices, systems and methods of the present disclosure are described with reference to the accompanying drawings. In the drawings, like reference numbers indicate identical or substantially similar elements.

FIGS. 10A-10C show coupling of the adaptor to the end effector, according to implementations of the present disclosure.

FIGS. 15A-15C show a modular insertion module, according to implementations of the present disclosure.

DETAILED DESCRIPTION

Figure 1A:
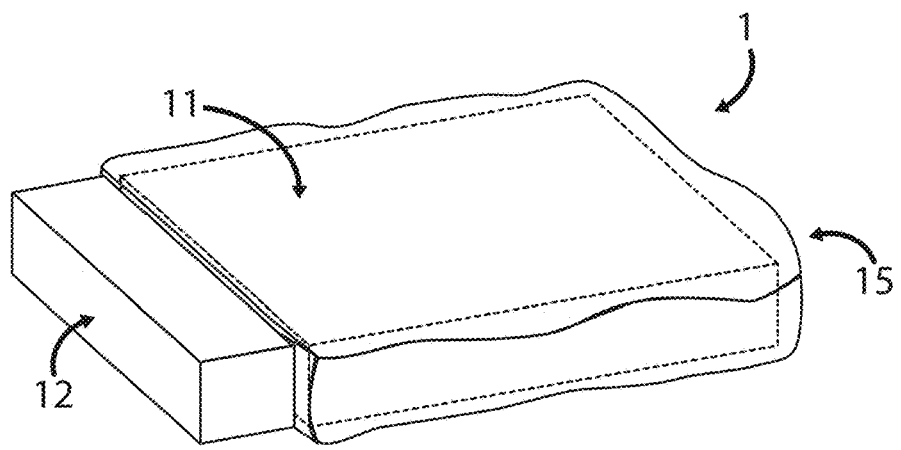
FIGS. 1A and 1B show schematic diagrams of automated medical devices having reusable and disposable parts, according to implementations of the present disclosure.
Figure 1B:
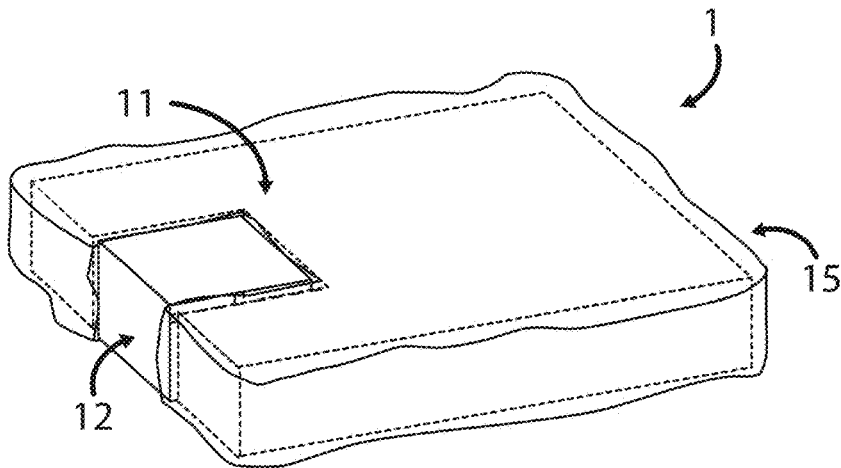

FIGS. 1A and 1B show schematic diagrams of automated medical devices 1 having reusable and disposable parts 11, 12, respectively, such that separation between the two parts is necessary for maintaining a sterile environment, as the disposable part is sterile, and the reusable part is typically non-sterile.

In some implementations, the reusable part 11 and the disposable part 12 are coupled to each other at one end, such that they are positioned end-to-end or side-by-side, as shown in FIG. 1A. In other implementations, the disposable part 12 may be received, at least in part, within the reusable part 11, as shown in FIG. 1B. The user covers the reusable part 11 with a sterile drape 15, to separate it from the sterile disposable part 12 and also prevent the medical staff and the patient from touching the reusable part 11. It can be appreciated that the automated device may have a plurality of reusable parts, as well as a plurality of disposable parts.

Figure 2:
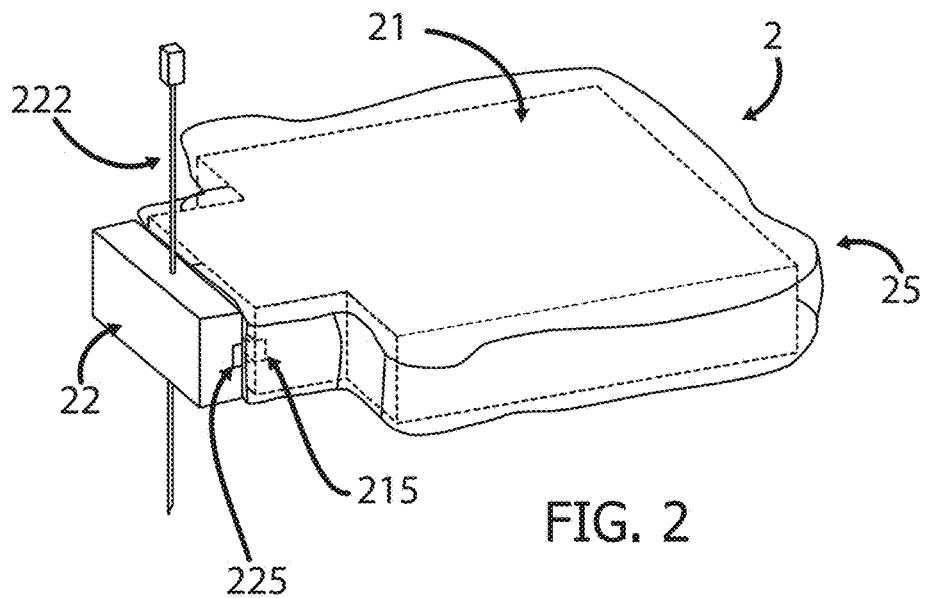
FIG. 2 shows a schematic diagram of an automated insertion device having reusable and disposable parts, according to implementations of the present disclosure.

FIG. 2 shows a schematic diagram of an automated medical device 2 for inserting a medical tool 222 into a subject's body, and having reusable and disposable parts 21, 22 respectively. The reusable part 21 may include the electronic components and the driving mechanism (not shown in FIG. 2), and the disposable part 22 may include the insertable medical tool 222, for example, a needle, introducer, port, etc., such that the disposable part 22 is discarded once the procedure is completed, and a new disposable part 22 is coupled to the reusable part 21 prior to the next procedure. In some implementations, the driving mechanism, which is in the reusable part 21, is controlled by the user to align the medical tool 222 with the chosen entry point and/or entry angle on the patient's body, whereas the insertion of the tool 222 into the patient's body is carried out by a separate insertion mechanism. The insertion mechanism may be located in the reusable part 21, in the disposable part 22, or divided between the reusable and disposable parts, such that a portion of the insertion mechanism 215 is located in the reusable part 21, and another portion of the insertion mechanism 225 is located in the disposable part 22. In case the insertion mechanism is divided between the reusable and disposable parts, operative coupling of the two portions 215, 225 is required in order for the insertion mechanism to become functional. In such a case, the sterile drape 25 separating between the reusable and the disposable parts 21, 22 must also be placed between the two portions of the insertion mechanism 215, 225, while enabling force and/or torque transfer between the two portions, and without compromising the sterile environment.

Figure 3:
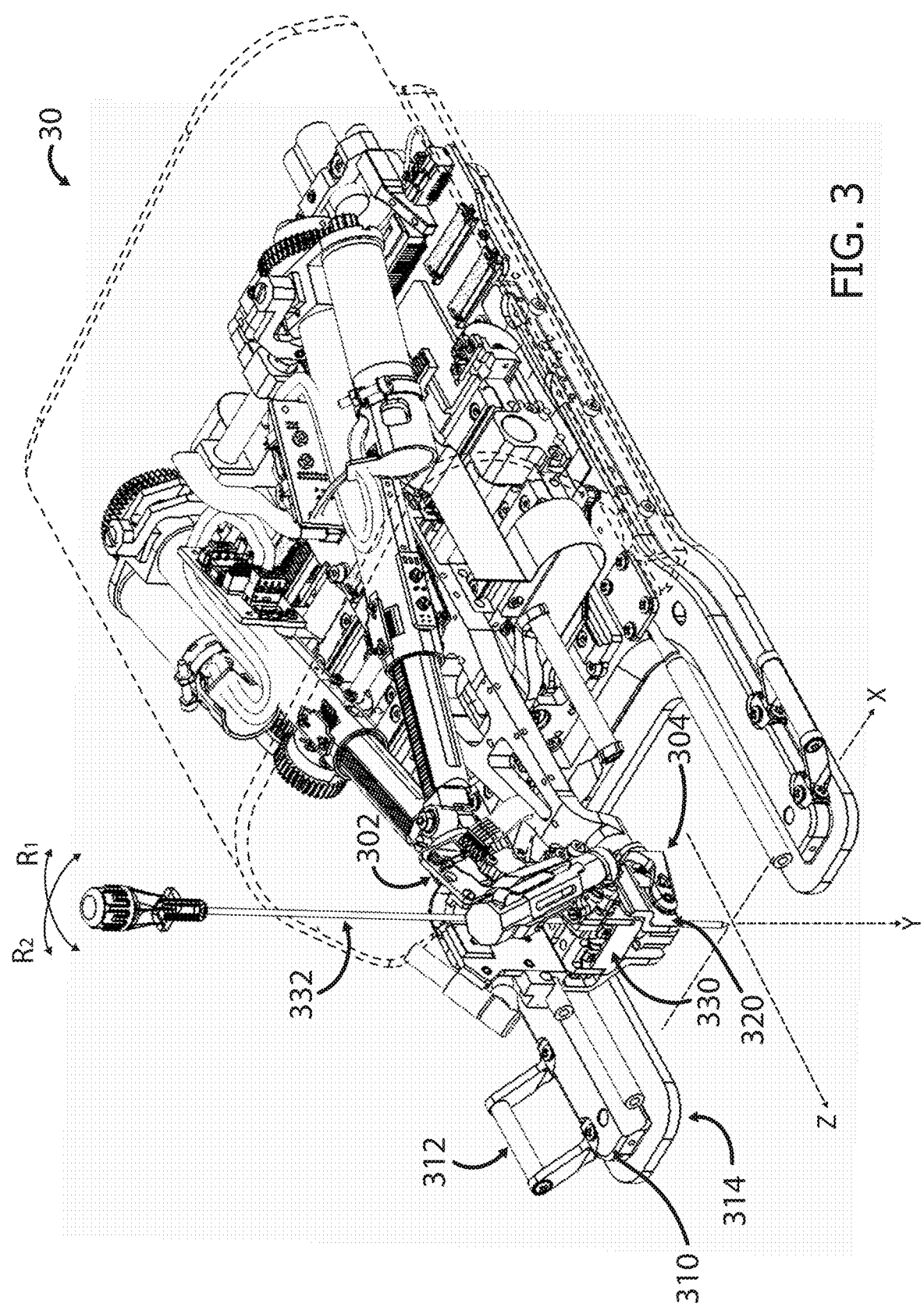
FIG. 3 shows an exemplary automated insertion device having reusable and disposable parts, according to implementations of the present disclosure.

FIG. 3 shows an exemplary automated insertion device 30 having reusable and disposable parts. In some implementations, the insertion device 30 is configured to be coupled to a dedicated arm or base which is secured to the patient's bed, to a cart positioned adjacent the patient's bed or to an imaging device, as described, for example, in U.S. Patent Application Publication No. 2016/0249990 to Glozman et al, for "Needle Steering by Shaft Manipulation", and in U.S. Patent Application Publication No. 2016/0249991, to Glozman et al, for "Gripper for Robotic Image Guided Needle Insertion", both of which are incorporated herein by reference in their entireties. In other implementations, the insertion device 30 is configured to be mounted on the subject's body, either directly or by means of a mediator base/plate (not shown). In such cases, the insertion device's base 310, or the mediator base, may be provided with anchors 312 for connecting straps (not shown in FIG. 3) which secure the device 30 to the patient's body, or with a mounting pad 314 which may include an adhesive layer (not shown) on its bottom surface, or with any other suitable means for attaching the device 30 to the patient's body, such as those described in co-owned International Patent Application Publication No. WO 2017/179044 to Arnold et al, for "Devices and Methods for Attaching a Medical Device to a Subject", incorporated herein by reference in its entirety.

In some implementations, the insertion device 30 may have five degrees of freedom (DOF): linear translation along the Z axis (front-back), linear translation along the X axis (left-right), rotation about the X axis (forward-backward) $R_1$ and rotation about the Z axis (left-right) $R_2$, and insertion, i.e., longitudinal needle translation substantially along the Y axis (when the needle is in the vertical position, as shown in FIG. 3). A similar device is described in detail in above-mentioned International Patent Application Publication No. WO/2017/203531. In such implementations, the insertion mechanism, i.e., the mechanism which executes the longitudinal translation of the medical tool, may be partly reusable and partly disposable. For example, the automated device 30 may include a reusable end effector 320, which may be coupled to the driving mechanism via one or more gimbals 302, 304, and a disposable insertion module 330, which includes the medical tool 332, and which is coupled to the end effector 320. The insertion mechanism may be divided between the end effector 320 and the insertion module 330, such that a portion of the insertion mechanism is reusable and a portion of the insertion mechanism is disposable, and the mechanism becomes functional only upon coupling the insertion module 330 to the end effector 320, as will be disclosed in detail hereinbelow.

Figure 4A:
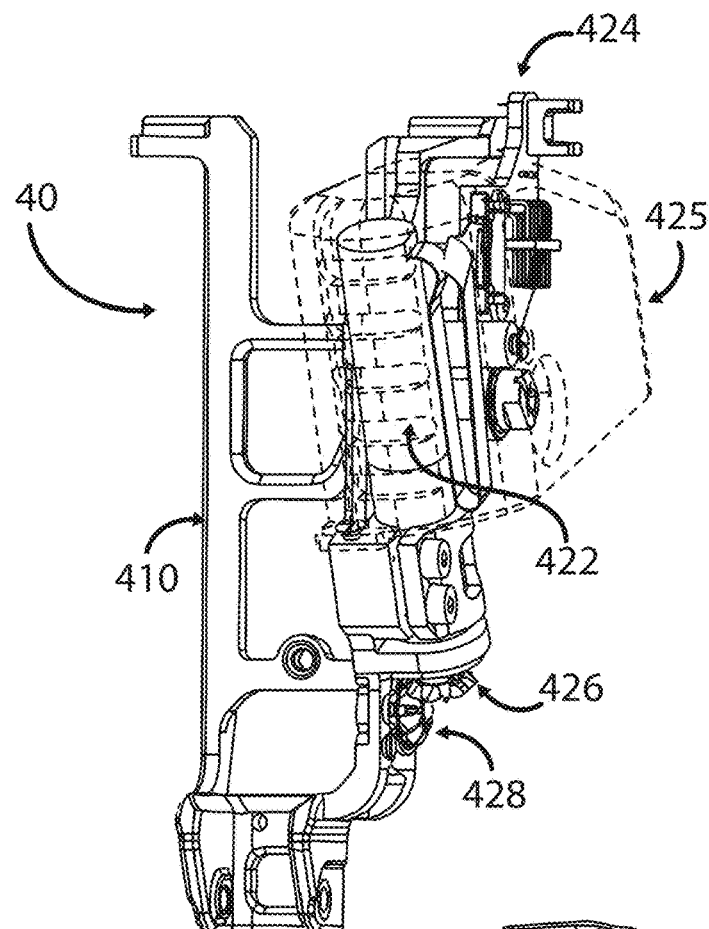
FIGS. 4A and 4B show perspective views of an exemplary end effector of an automated insertion device, according to implementations of the present disclosure.
Figure 4B:
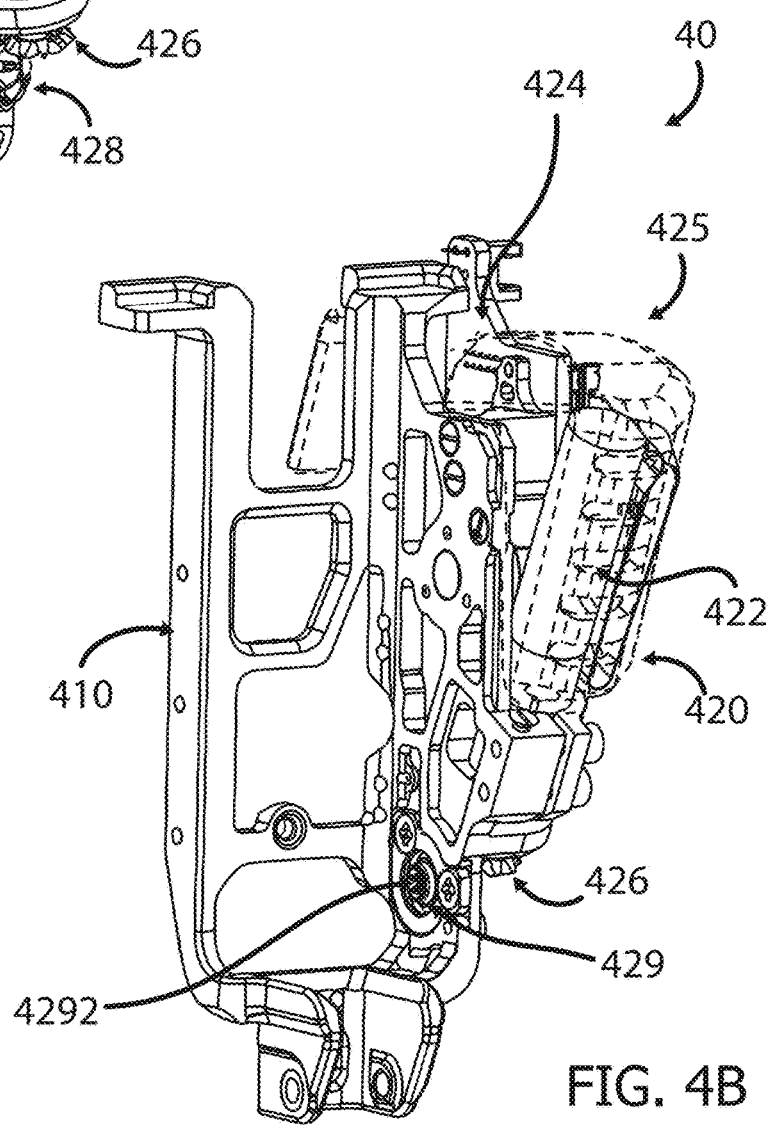

FIGS. 4A and 4B show perspective views of an exemplary end effector 40 of an automated insertion device. The end effector 40 may include a body (or "housing") 410 and a motor assembly 420 attached externally to the end effector body 410. The motor assembly 420 may constitute the reusable portion of the insertion mechanism. The end effector body 410 may be configured to receive and house the insertion module (not shown in FIGS. 4A and 4B), which is preferably a disposable single-use unit, such that the end effector 40 can be used repeatedly with new disposable insertion modules.

The end effector's motor assembly 420 may include an actuator, such as a geared motor 422 provided with a motor encoder (not shown), and a Printed Circuit Board (PCB) 424, which includes the electronic components of the insertion mechanism. The motor assembly 420 may further include gears, such as a bevel gear 426, which may engage with a second bevel gear 428, which is coupled to the end effector body 410. In some implementations, the motor 422 and the PCB 424 may be shielded by a motor cover 425, and the two bevel gears 426, 428 may be shielded by a gear cover (not shown in FIGS. 4A-4B). As shown in FIG. 4B, in some implementations the bevel gear 428 may be rigidly coupled to a cylinder 429, which rotates together with the gear 428, to transfer torque to a second portion of the insertion mechanism (not shown in FIG. 4B), which is located in the insertion module. The cylinder 429 may be configured to receive the tip of the insertion module's drive axis (not shown in FIG. 4B), and it may be provided with inner ridges 4292, which engage with corresponding outer ridges (or—teeth) of the drive axis' tip, such that the drive axis rotates together with the bevel gear 428 (hereinafter also referred to as "female bevel gear") and the cylinder 429, resulting in activation of the second portion of the insertion mechanism located in the insertion module, as will be described in detail hereinbelow.

In some implementations, the bevel gear 428 may include an extending axis with a bearing, to constrain the bevel gear's lateral movement and thus provide stabilization to the insertion mechanism.

It can be appreciated that any other applicable method of transferring torque from the motor assembly 420 to the insertion module may be otherwise implemented. Further, in some implementations, only a portion of the motor assembly is coupled to the end effector 40. For example, in some implementations, the motor may be located at a rear location of the device, and it may activate the portion of the motor assembly which is coupled to the end effector 40 using a timing belt.

Figure 5A:
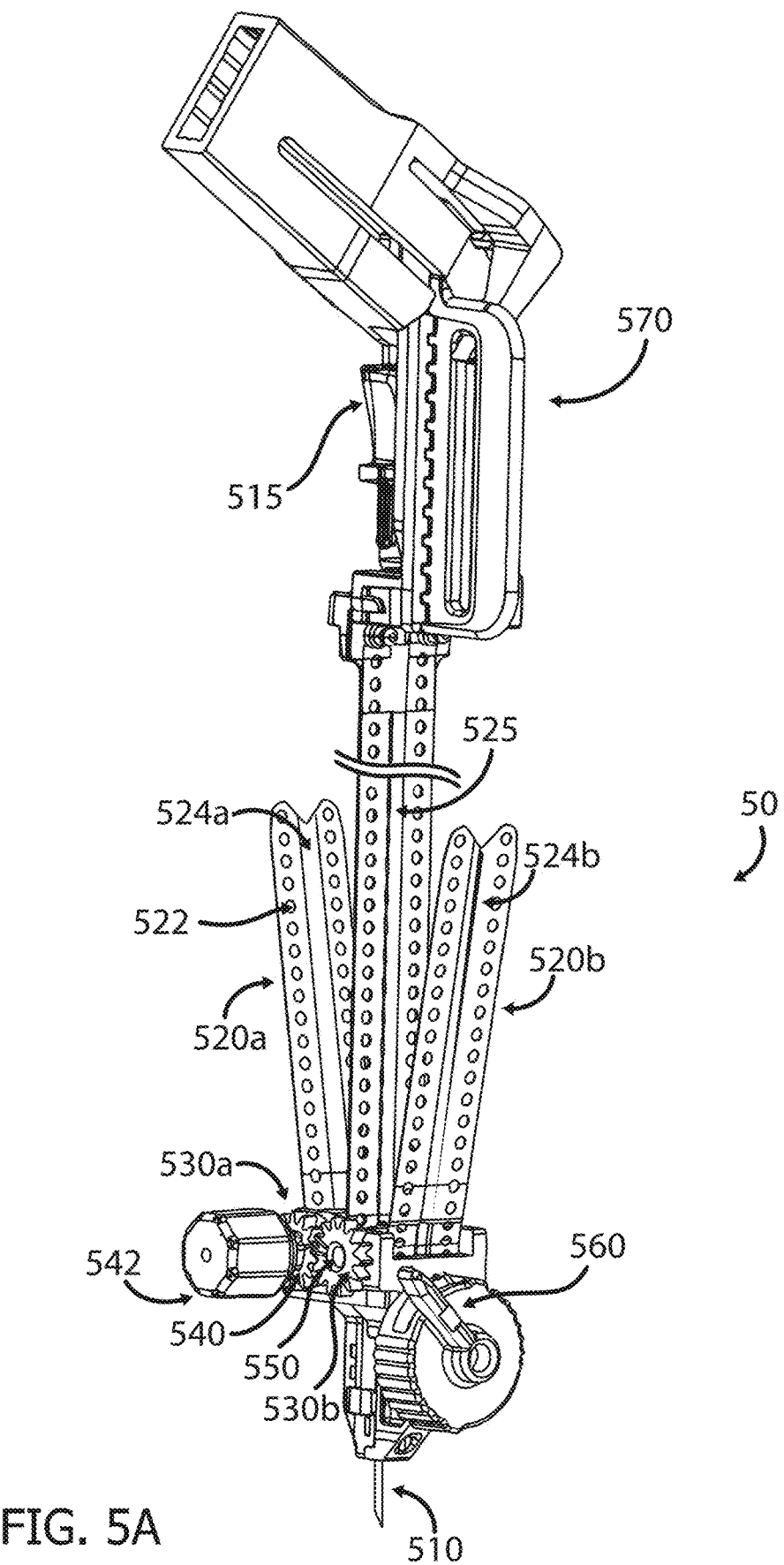
FIGS. 5A and 5B show perspective views of an exemplary insertion module of an automated insertion device, according to implementations of the present disclosure.
Figure 5B:
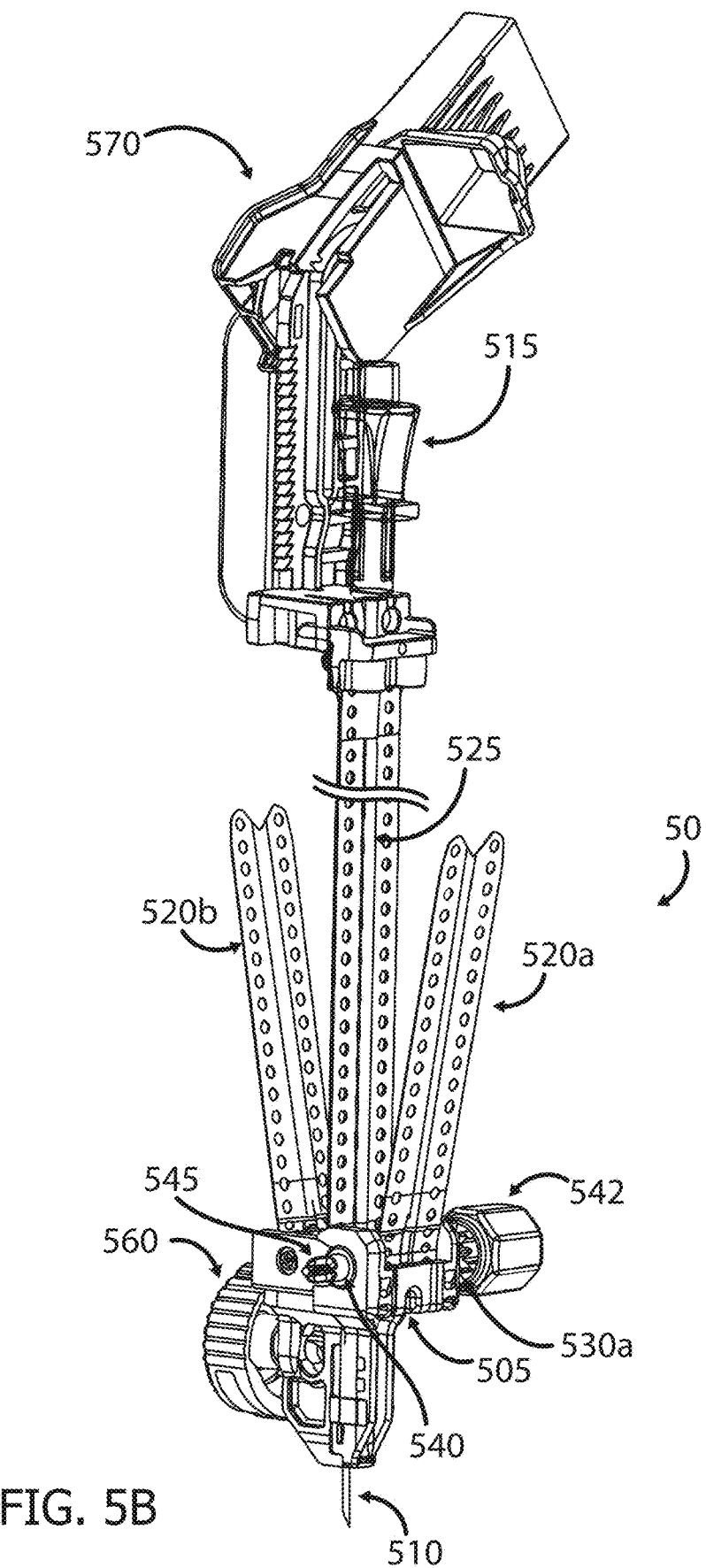

FIGS. 5A and 5B show perspective views of an exemplary insertion module 50 of an automated insertion device. The insertion module 50 may comprise a needle 510, or any other insertable tool, such as an introducer, a catheter, etc., enclosed within a channel 525 formed by two flexible strips 520a, 520b coupled together. In some implementations, the needle 510 is provided together with the insertion module 50, whereas in other implementations, the insertion module 50 is configured for receiving a variety of different commercially available needle types, and the needle is chosen and introduced into the insertion module by the user (e.g., nurse, physician) prior to initiating the insertion procedure. The flexible strips 520a, 520b, which are part of the insertion mechanism, may have perforations 522 running along at least a portion of their length, and a groove 524a, 524b, respectively, running along their longitudinal centerline, such that when the strips 520a, 520b are attached to each other, their coupled grooves 524a, 524b form together the channel 525 which receives and encloses the needle 510.

The insertion module 50 may further comprise two rollers (not shown in FIGS. 5A-5B), which engage with the strips 520a, 520b to advance the needle 510 toward the patient's body, as will be described in detail hereinbelow. One of the rollers may be mounted on the drive axis 540 and the other roller on an axis 550 parallel to the drive axis. As previously described, the drive axis 540 rotates together with the end effector's female bevel gear, once its tip 545, shown in FIG. 5B, is received within the female bevel gear. Thus, rotation of the female bevel gear causes the roller mounted on the drive axis to rotate in the same direction as the female bevel gear. The insertion module 50 may further include two gears 530a, 530b which are mounted on the two abovementioned axes, at the end opposite the drive axis' tip 545. Rotation of the drive axis 540 rotates gear 530a in the same direction as the drive axis, which in turn rotates gear 530b in the opposite direction, via engagement between the two gears 530a, 530b, resulting in counter-rotation of the two rollers. The roller mounted on the drive axis 540 will be referred to hereinafter as the "drive roller", and the second roller will be referred to hereinafter as the "driven roller".

Further shown in FIGS. 5A-5B are an activation knob 542 and a tightening knob 560. The activation knob 542 may be used to establish operative coupling between the drive axis' tip 545 and the end effector's female bevel gear, as will be described in detail hereinbelow.

The tightening knob 560 may be used to tighten and secure the coupling between the insertion module and the drape adaptor (not shown in FIGS. 5A-5B), and, in some implementations, also with the end effector, as will be described in detail hereinbelow. FIG. 5B further shows a niche 505 located in the back portion of the insertion module 50, which is configured to receive a dedicated protrusion in the drape adaptor (not shown in FIG. 5B), to ensure proper positioning of the insertion module 50 within the adaptor and/or to establish a rigid coupling between the insertion module 50 and the drape adaptor, as will be described in detail hereinbelow.

In some implementations, the insertion module 50 may include a needle head holder 570, which secures together the needle head 515 and the proximal end of the strips 520a, 520b, such that pulling of the strips toward the patient's body, via counter-rotation of the rollers, results in advancement of the needle 510 toward the patient's body. The holder 570 may be adapted to receive a variety of needle types having different needle gauges and needle heads of different shapes and sizes, to avoid limiting the user to a single needle type or requiring the user to carry multiple holders, each compatible with a specific needle type, as described, for example, in co-owned International Patent Application Publication No. WO/2018/055621 to Galili et al, for "Universal Holder for an Insertable Medical Tool", incorporated herein by reference in its entirety.

Figure 6A:
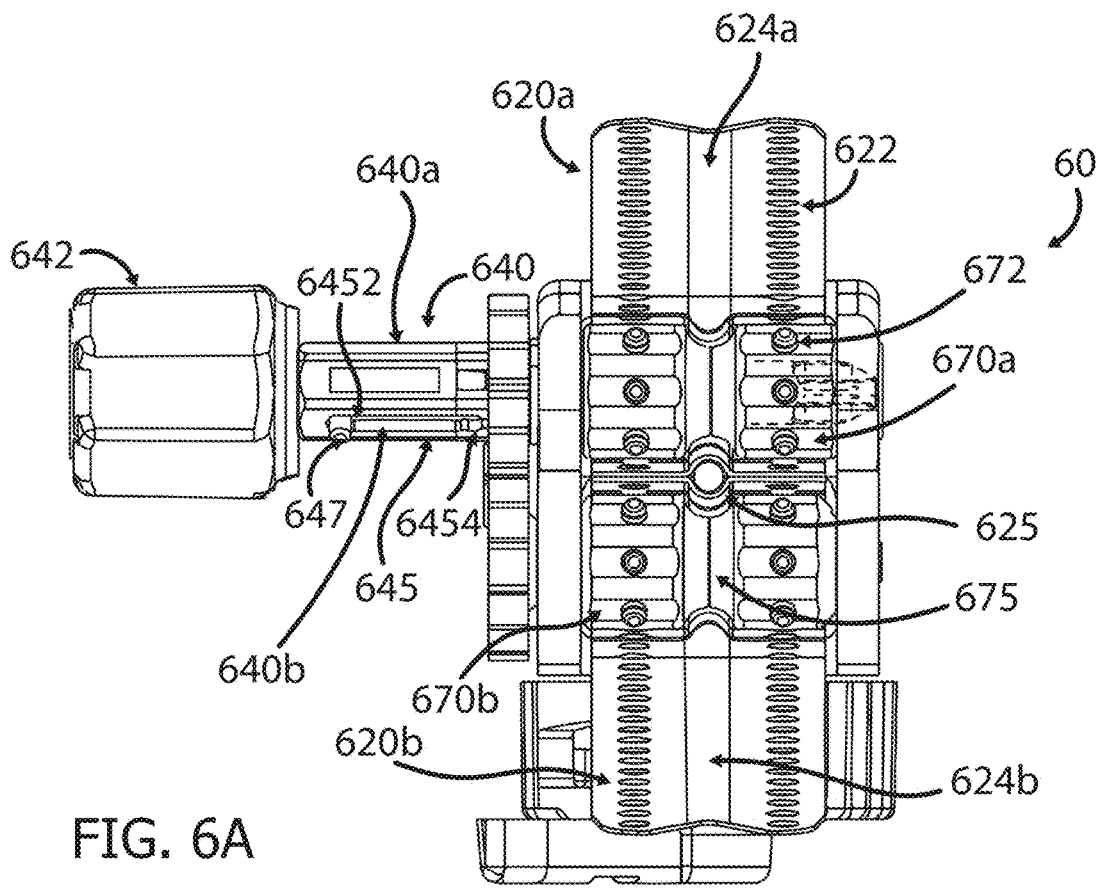
FIGS. 6A and 6B show top views of the exemplary insertion module of FIGS. 5A-5B.
Figure 6B:
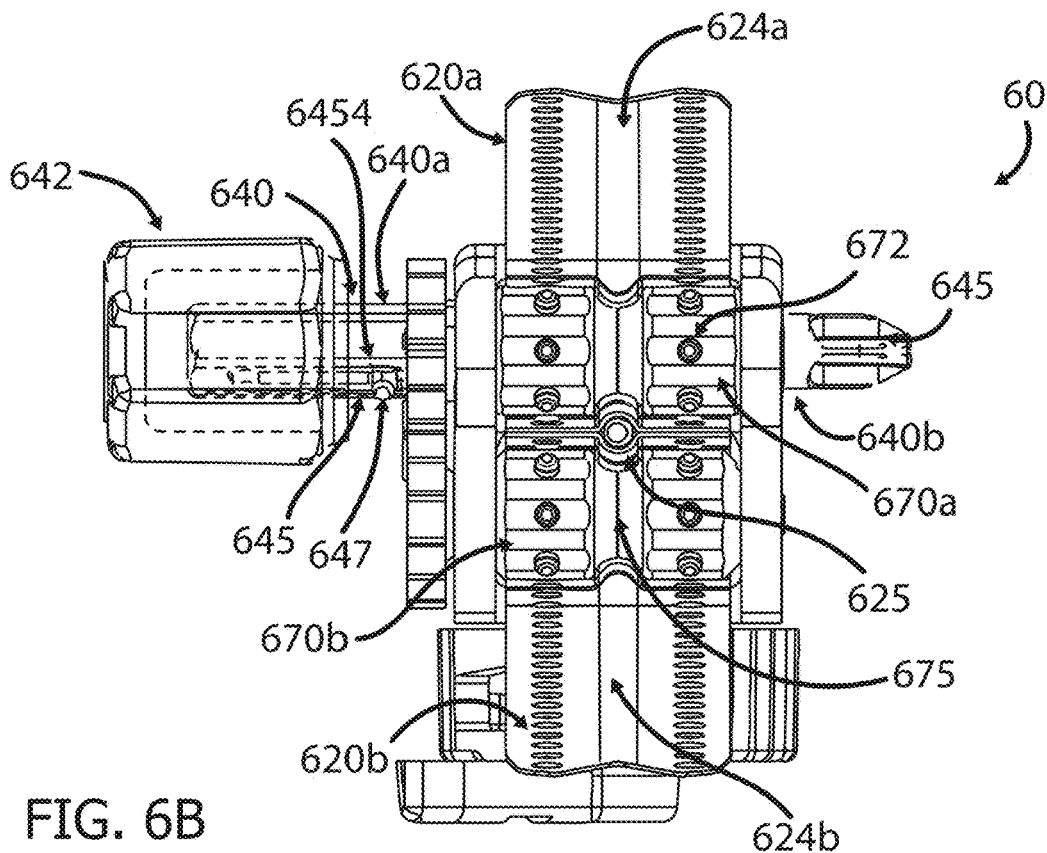

FIGS. 6A and 6B show top views of the exemplary insertion module 60 of FIGS. 5A-5B. FIG. 6A shows the insertion module 60 prior to coupling of the drive axis 640 to the female bevel gear of the end effector, with the drive axis 640 being in the retracted position.

In some implementations, the drive axis 640 may be a two-part drive axis, having outer and inner parts, 640a and 640b, respectively, which may be coaxial. The outer part 640a of the drive axis may be hollow and have the drive roller 670a mounted thereon, and the inner part 640b of the drive axis may be positioned within the outer part 640a and linearly moveable between a retracted position, as shown in FIG. 6A, and an extended position, as shown in FIG. 6B.

The inner part 640b of the drive axis 640 may include the knob 642 at one end and the drive axis' tip 645 at the opposite end, such that moving the inner part 640b to the extended position by pushing and/or rotating the knob 642, results in the tip 645 being operatively coupled to the female bevel gear of the end effector, rendering the insertion mechanism functional.

In some implementations, the outer part 640a of the drive axis may include at least one slot 645 having two receiving ends, such as snap-in niches 6452, 6454, and the inner part 640b may include a protrusion 647, which is received by the snap-in niche 6452 when the drive axis is in the retracted position, and by snap-in niche 6454 when the drive axis is in the extended position. In this example, the coupling between the protrusion 647 and each of the snap-in niches 6452, 6454 is a snap-fit coupling, which prevents the inner part 640b to move relative to the outer part 640a. This is to ensure that the inner part 640b of the drive axis 640 remains in the retracted position until the user actively moves it into the extended position after coupling the insertion module 60 to the drape adaptor, and that after being moved to the extended position, the inner part 640b of the drive axis 640 remains in the extended position, and rotates together with the outer part 604a upon activation of the insertion mechanism.

Once the insertion mechanism is activated by the user, the motor (not shown in FIGS. 6A-6B) rotates the first bevel gear (not shown in FIGS. 6A-6B), which in turn rotates the female bevel gear (not shown in FIGS. 6A-6B). Via engagement of the tip 645 of the insertion module's drive axis 640 with the female bevel gear, the drive axis 640 rotates together with the female bevel gear. Since the drive roller 670a and the gear 630a are mounted on the drive axis 640, the drive roller 670a and the gear 630a rotate together with the drive axis. the gear 630a in turn rotates the gear 630b, which is mounted on the parallel axis together with the driven roller 670b, in the opposite direction, resulting in counter-rotation of the two rollers 670a, 670b. As the rollers 670a, 670b counter-rotate, their protrusions 672 engage the strips' perforations 622, such that the strips 620a, 620b, together with the enclosed needle, are pulled in the distal direction towards the patient's body. The strips 620a, 620b are then forcefully separated from one another, pulled in opposite directions and around the rollers 670a, 670b, while the needle continues its translation in the distal direction and into the body of the patient.

Also shown in FIGS. 6A-6B is the channel 625 formed by the coupling of the tubular grooves 624a, 624b of the strips 620a, 620b, respectively, and the annular groove 675 in each of the rollers 670a, 670b, designed to allow uninterrupted passage of the channel 625 between the rollers as the strips 620a, 620b move in the distal direction and around the rollers 670a, 670b.

Figure 7A:
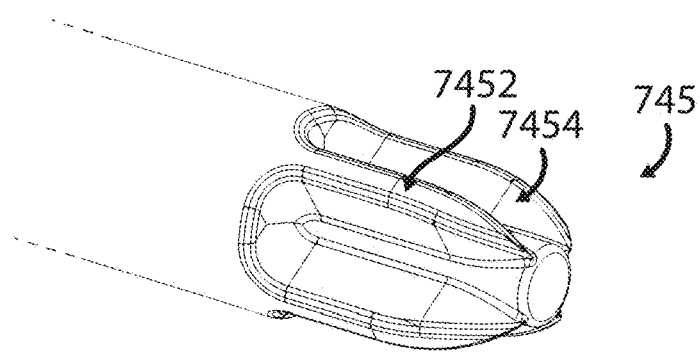
FIG. 7A shows a perspective view of the tip of the drive axis of the insertion module of FIGS. 5A-5B, according to implementations of the present disclosure.
Figure 7B:
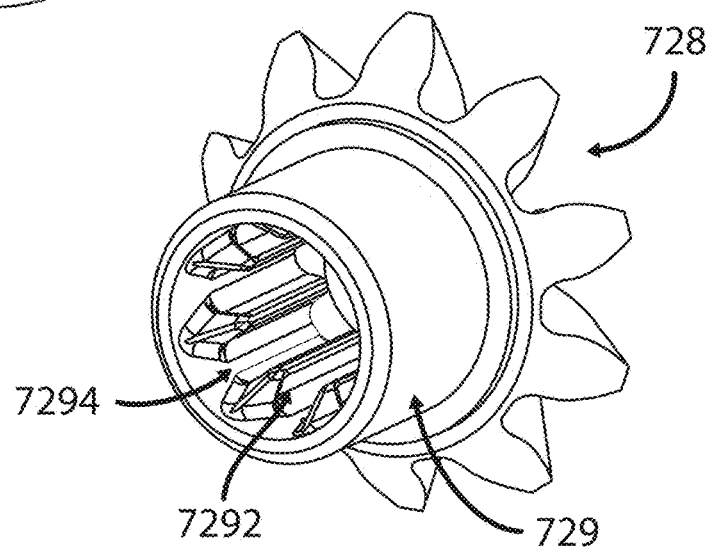
FIG. 7B shows a perspective view of the female bevel gear of the end effector of FIGS. 4A-4B, according to implementations of the present disclosure.

FIG. 7A shows a perspective view of the tip 745 of the drive axis. The tip 745 may include a plurality of outer ridges 7452 (or—"longitudinal teeth") spaced apart along the circumference of the tip 745, with grooves 7454 therebetween. In some implementations, the tip 745 may be substantially cone shaped, to facilitate insertion into the cylinder 729 of the female bevel gear 728 shown in FIG. 7B.

Figure 7C:
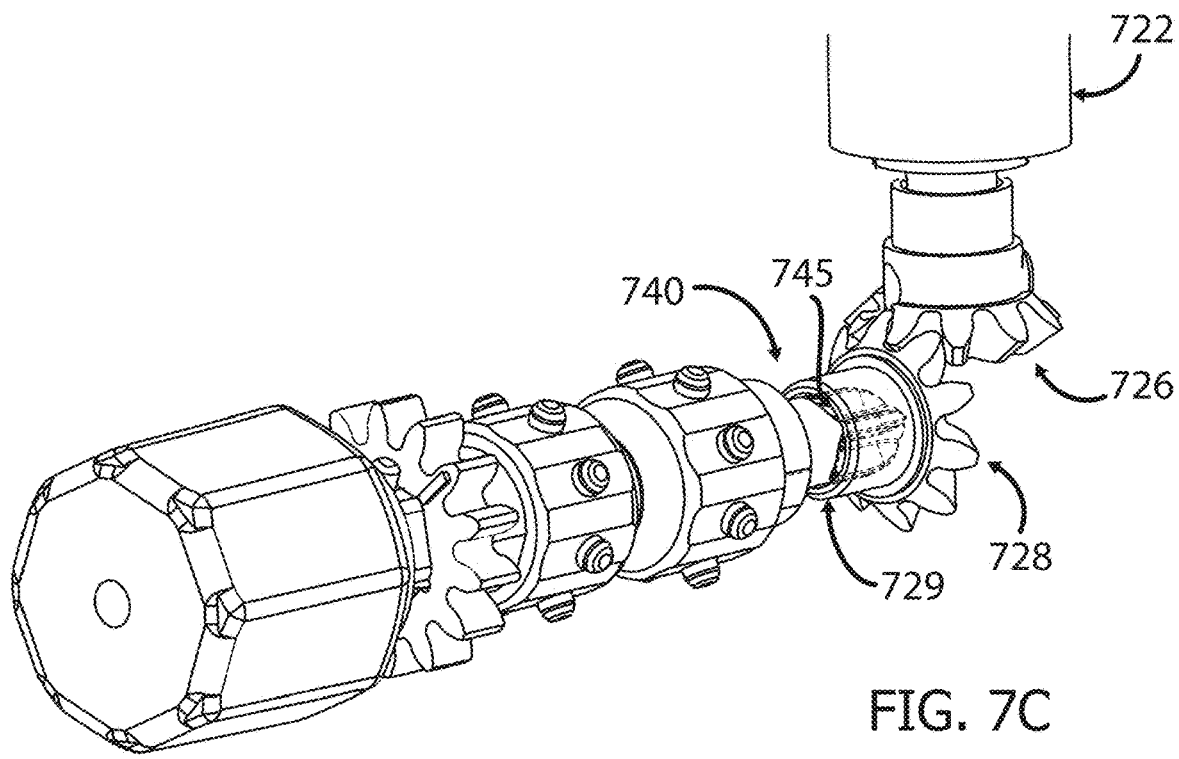
FIG. 7C shows the tip of the drive axis of FIG. 7A coupled to the female bevel gear of FIG. 7B, according to implementations of the present disclosure.

The cylinder 729 of the end effector's female bevel gear 728 may include inner grooves 7294, defined by inner ridges 7292, which are generally uniformly disposed along the circumference of the cylinder 729 and spaced apart such that aligned engagement between the outer ridges 7452 of the tip 745 and the inner grooves 7294 of the cylinder 729 is achieved regardless of the tip's rotational orientation. FIG. 7C shows the drive axis' tip 745 and the female bevel gear's cylinder 729 coupled together, resulting in the insertion mechanism becoming functional. Activation of the geared motor 722 will now rotate the bevel gear 726, which in turn will rotate the female bevel gear 728 and thus the drive axis 740, via engagement of the tip 745 with the female bevel gear's cylinder 729.

Figure 8:
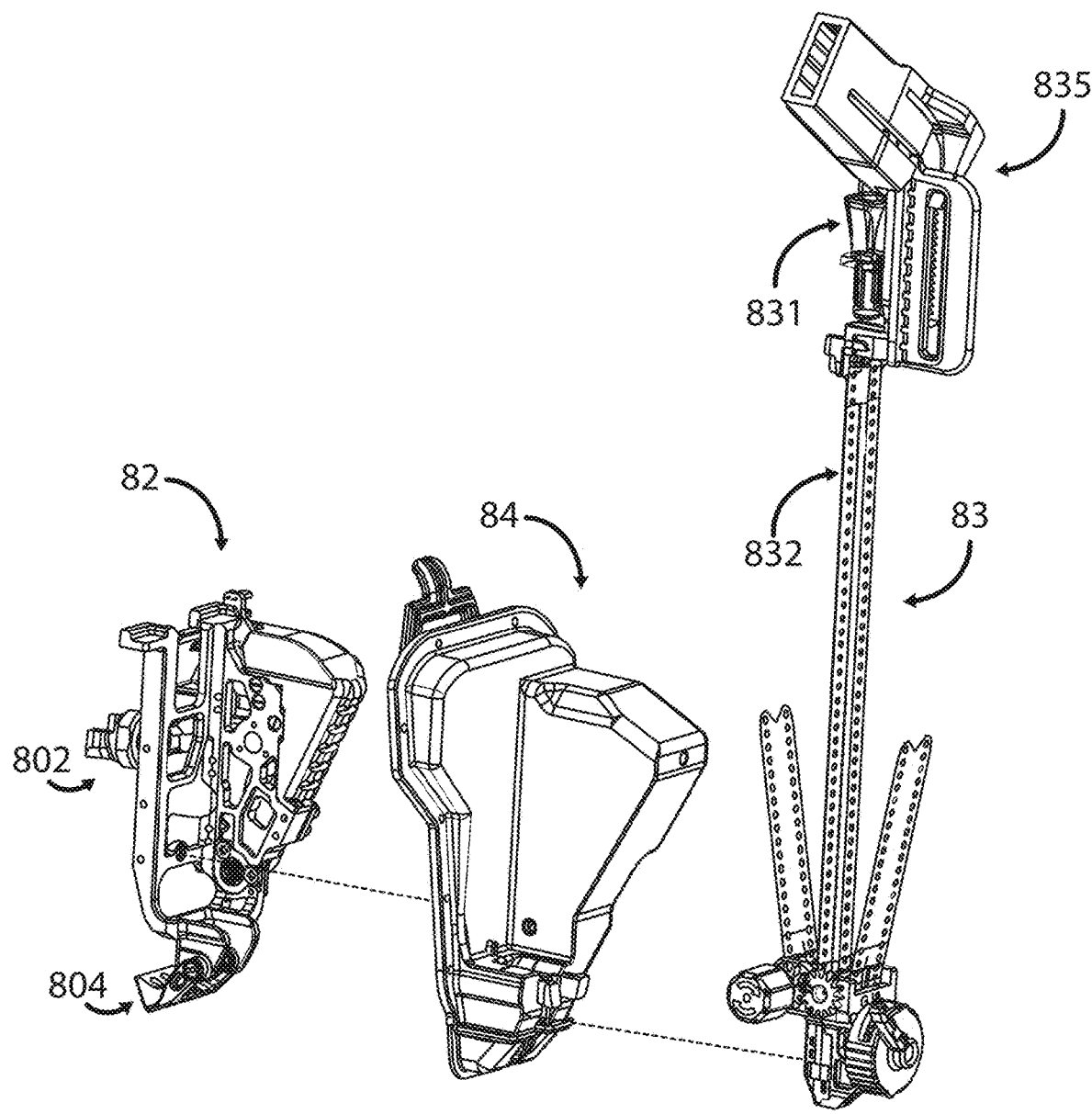
FIG. 8 shows an exploded view of an end effector, insertion module and drape adaptor, according to implementations of the present disclosure.

FIG. 8 shows an exploded view of the end effector 82, insertion module 83 and an exemplary drape adaptor 84. The end effector 82 is shown with the two gimbals 802, 804 which may be utilized for coupling the end effector 82 to the driving mechanism of the insertion device. The insertion module 83 may include a needle head holder 835, which secures together the needle head 831 and the proximal end of the strips 832. In some implementations, the drape adaptor 84 is coupled to the end effector 82 and the insertion module 83 is then coupled to the drape adaptor 84. Alternatively, the insertion module 83 may be coupled first to the drape adaptor 84, either by the user prior to the medical procedure or pre-assembled by the manufacturer/distributer, and the coupled units may then be coupled, by the user, to the end effector 82. In further implementations, the drape adaptor 84 and the insertion module 83 may be designed and manufactured as a single integral unit, which is coupled to the end effector 82 by the user prior to the medical procedure. Once the end effector 82, drape adaptor 84 and insertion module 83 are coupled together, the tip of the drive axis of the insertion module 83 can be received within the female bevel gear of the end effector 82, through the drape adaptor 84, and torque can be transferred to the portion of the insertion mechanism positioned in the insertion module 83 without compromising the sterility of the insertion module 83.

Figure 9A:
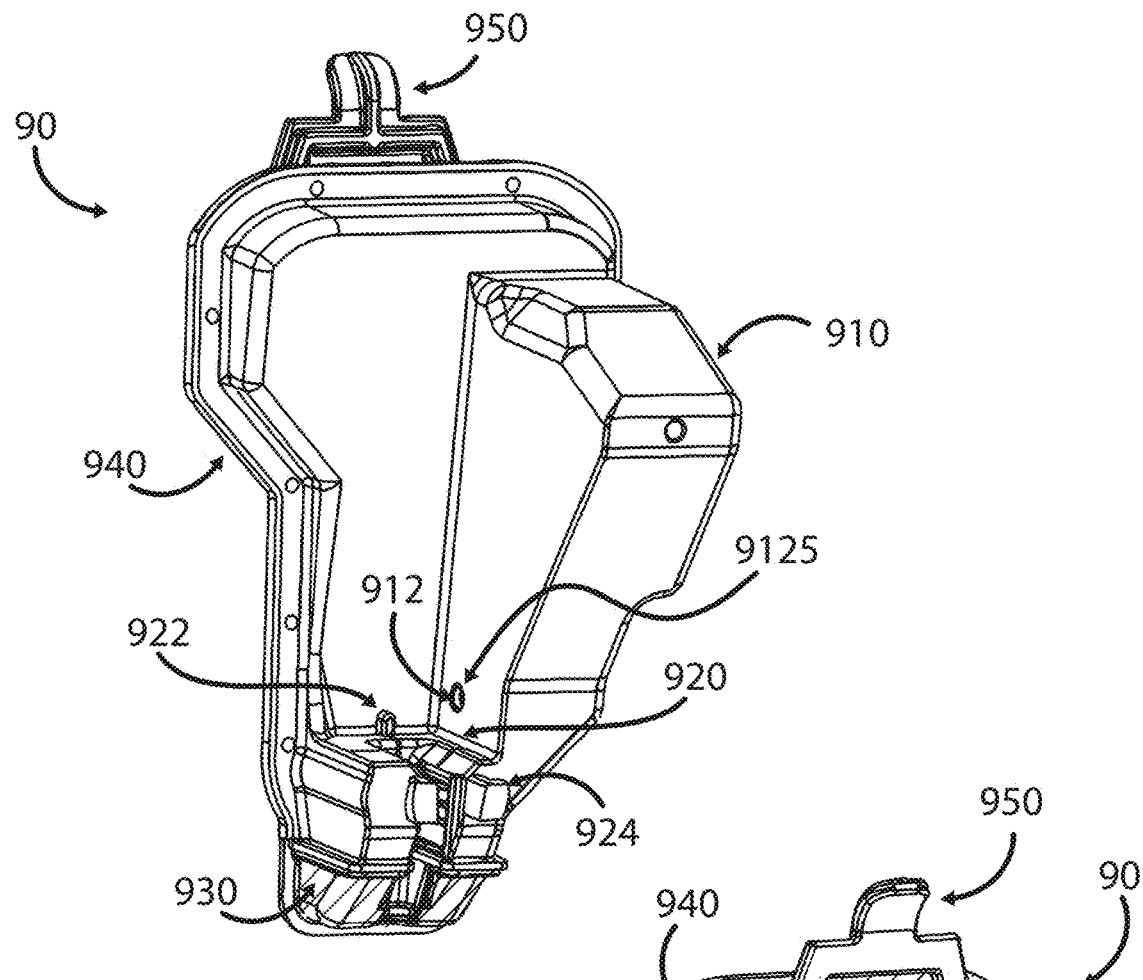
FIGS. 9A and 9B show front (FIG. 9A) and back (FIG. 9B) perspective views of a drape adaptor, according to implementations of the present disclosure.

FIG. 9A shows a front perspective view of the drape adaptor 90. The drape adaptor 90 may be adapted to be coupled to the end effector, and cover it, at least in part. In some implementations, the drape adaptor 90 may further be configured to receive the insertion module, or, in alternative implementations, the drape adaptor 90 and the insertion module may be manufactured as a single unit. The drape adaptor 90 may include a projecting section 910 to cover the motor assembly of the end effector. The projecting section 910 may include an opening 912 through which the drive axis of the insertion module can pass, to enable its operative coupling with the end effector's female bevel gear, upon moving the drive axis from the retracted position to the extended position.

In order to prevent any possible leakage of contaminants through the opening 912 into the sterile environment, the opening 912 may be provided with a sealing member 9125, such as an O-ring, overmold elastomeric material, etc., which closes on the inserted drive axis. The adaptor 90 may further include a receiving section 920 for receiving the insertion module and securing it thereto. The back end of the receiving section 920 may include an alignment member, such as a protrusion 922, which fits within the niche located in the back portion of the insertion module (shown in FIG. 5B) when the insertion module is coupled to the drape adaptor 90.

The insertion module may be modular, such that it has a plurality of separable parts. For example, the insertion module may include two separable parts; a rear part, which includes the drive roller, and a front part, which includes the driven roller, as will be described hereinbelow. The two-part configuration allows the user to disconnect the two parts of the insertion module from each other, and remove them from the needle, while leaving the needle inserted within the patient's body, as disclosed in abovementioned U.S. Patent Application Publication No. 2017/0258489. In such implementations, the coupling between the protrusion 922 and the niche of the insertion module may be rigid such that it prevents decoupling the rear part of the insertion module from the adaptor 90, thus allowing disconnection of only the front part of the insertion module. Alternatively, the coupling between the protrusion 922 and the niche may serve for alignment only, i.e., to ensure proper positioning of the insertion module within the receiving portion 920 of the adaptor 90, and decoupling of the rear part of the insertion module from the adaptor is prevented using other means, as will be described in further detail hereinbelow.

The receiving portion 920 may further include at least a portion of a mechanism for tightening the coupling between the insertion module and the drape adaptor, following insertion of the insertion module into the adaptor's receiving portion 920. In some implementations, the tightening mechanism may include a tightening knob, such as the tightening knob shown in FIGS. 5A-5B, and one or more capturing members 924, which capture corresponding capturing members of the tightening knob (not shown in FIG. 9A), upon rotation of the tightening knob, as will be described in detail hereinbelow.

In some implementations, the adaptor 90 may be manufactured from a substantially rigid material, such as Polycarbonate (E.g., P C Makrolon 2458 by Bayer A G of Germany), Polyamide (e.g., GV-5H by EMS-Grivory of Switzerland), Acrylonitrile Butadiene Styrene (ABS) (e.g., Magnum 8391 by Trinseo L L of the U.S.A) or any other suitable material.

As discussed hereinabove, the end effector may be coupled to the insertion device via one or more gimbals, such as the gimbals shown in FIG. 3. In such implementations, the adaptor 90 may include a bottom section 930 to cover the insertion device's bottom gimbal upon coupling of the adaptor 90 to the end effector, and the bottom section 930 may be manufactured from a substantially elastic material, such as TM4ADT by Kraiburg TPE GmbH & Co. KG of Germany, or any other suitable thermoplastic elastomer (TPE), to allow free movement of the bottom gimbal, while limiting the size of the bottom section 930 so as to minimize contact of the drape adaptor 90 with the patient's skin.

In some implementations, the adaptor 90 may include a frame 940, which may be manufactured from a substantially elastic material, such as that of which the bottom section 930 is manufactured. The frame 940 may surround the entire adaptor 90, so as to provide a uniform surface for attaching the adaptor 90 to the drape sheet (not shown in FIG. 9A). In some implementations, the frame 940 and the bottom portion 930 of the adaptor 90 may be manufactured together as a single unit.

In some implementations, the adaptor 90 may further include at least one release handle 950 used for disconnecting the adaptor 90 from the end effector.

Figure 9B:
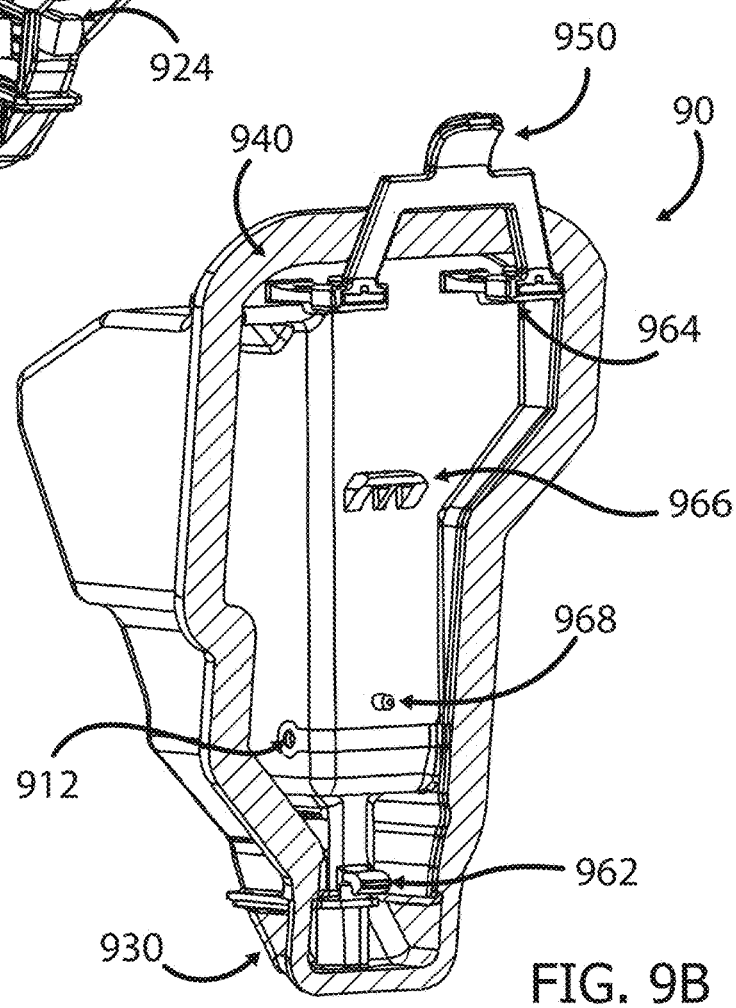

FIG. 9B shows a back perspective view of the drape adaptor 90. The drape adaptor 90 may include several elements at its back side for properly and securely coupling the adaptor 90 to the end effector. In some implementations, the adaptor 90 may include a gripper 962. The gripper 962 may be positioned at the lower part of the adaptor 90, such that coupling of the adaptor 90 to the end effector is carried out by placing the gripper 962 onto a dedicated bar (shown in FIG. 10B) of the end effector, to anchor the gripper 962 on the bar, and the upper part of the adaptor 90 can then be moved toward the upper part of the end effector via a pivoting movement, as shown in FIGS. 10A-10B hereinbelow.

The adaptor 90 may further include one or more latches 964, which establish a snap-fit connection with corresponding connectors (not shown in FIG. 9B) in the end effector, once the pivoting movement has been completed.

In some implementations, the end effector may include at least one auxiliary member (not shown), to facilitate establishing the snap-fit connection between the adaptor's latches 964 and the end effector's connectors. The auxiliary member/s may be, for example, small extension/s to the end effector body, to which the user may apply pressure with his/her fingers, from the back side of the end effector body, as he/she pushes the upper part of the adaptor 90 against the end effector body, until the snap-fit connection is established.

Since the end effector is non-sterile, contact between the user and the auxiliary members should be established only after the user wears sterile gloves and the auxiliary members are covered by the sterile drape.

It can be appreciated that the connection between the adaptor 90 and the end effector is not limited to a snap-fit connection, and that different auxiliary members may be employed to facilitate coupling the adaptor 90 to the end effector.

The latches 964 may be coupled to the release handle 950, which is pulled by the user to release the latches 964 from the connectors and thus enable removal of the adaptor 90 from the end effector. In some implementations, the adaptor 90 may further include one or more positioning members 966, 968 to ensure correct placement of the adaptor on the end effector and its stability.

In some implementations, the drape adaptor 90 may further include one or more fiducial markers (not shown), or any other suitable registration element/s, disposed at specific locations on the drape adaptor 90, for registration of the medical device to the image space, following coupling of the adaptor 90 to the end effector, in image guided procedures. Positioning registration element/s on the drape adaptor 90, i.e., adjacent the medical tool, enables determining the medical device's position relative to the image space during the procedure, without having to scan the entire device, but only a limited portion which includes the registration element/s, thus minimizing the exposure of the patient and the medical staff to radiation.

FIGS. 10A-10C show the adaptor 100 being coupled to the end effector 300. FIG. 10A shows the first stage of the coupling, in which the user couples the bottom portion of the adaptor 100 to the bottom portion of the end effector 300 by placing the adaptor's gripper 1062 on the anchoring bar 302 of the end effector. Once the gripper 1062 is anchored on the anchoring bar 302, as shown in cross-sectional view in FIG. 10B, the user pivots the adaptor 100 about the bar axis until the latches 1064 are captured by corresponding connectors 304 of the end effector 300, establishing a snap-fit connection. Auxiliary member/s (not shown) may be provided on the end effector body to facilitate establishment of the snap-fit connection. It can be appreciated that a snap-fit connection is merely one example of a mechanism to establish a durable connection of the adaptor 100 to the end effector 300. FIG. 10C shows the adaptor 100 coupled to the end effector 300. As shown, upon coupling the adaptor 100 to the end effector 300, the bottom gimbal 650, by which the end effector 300 may be coupled to the insertion device, together with the top gimbal 670, may be covered by the elastic bottom section 1030 of the adaptor 100. Manufacturing the adaptor's bottom section 1030 from elastic material allows free movement of the bottom gimbal, while limiting the size of the adaptor's bottom section 1030, and thus minimizing the contact of the drape adaptor 100 with the patient's skin.

Figure 11A:
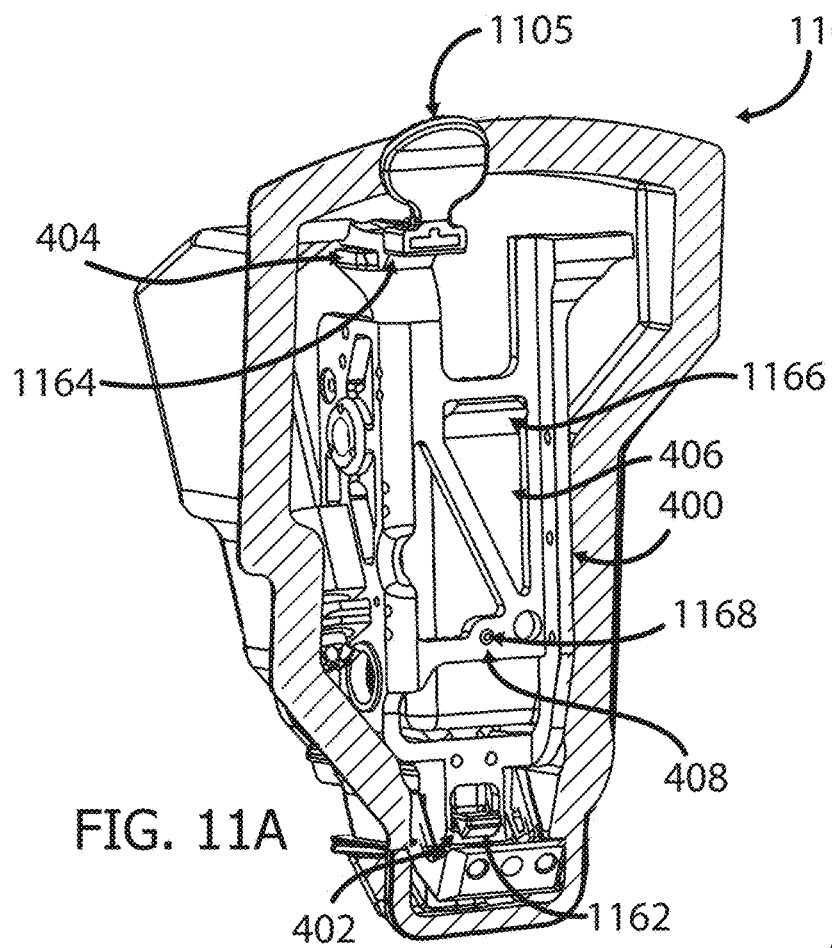
FIGS. 11A-11B show perspective back views of exemplary end effectors and drape adaptors coupled thereto, according to implementations of the present disclosure.
Figure 11B:
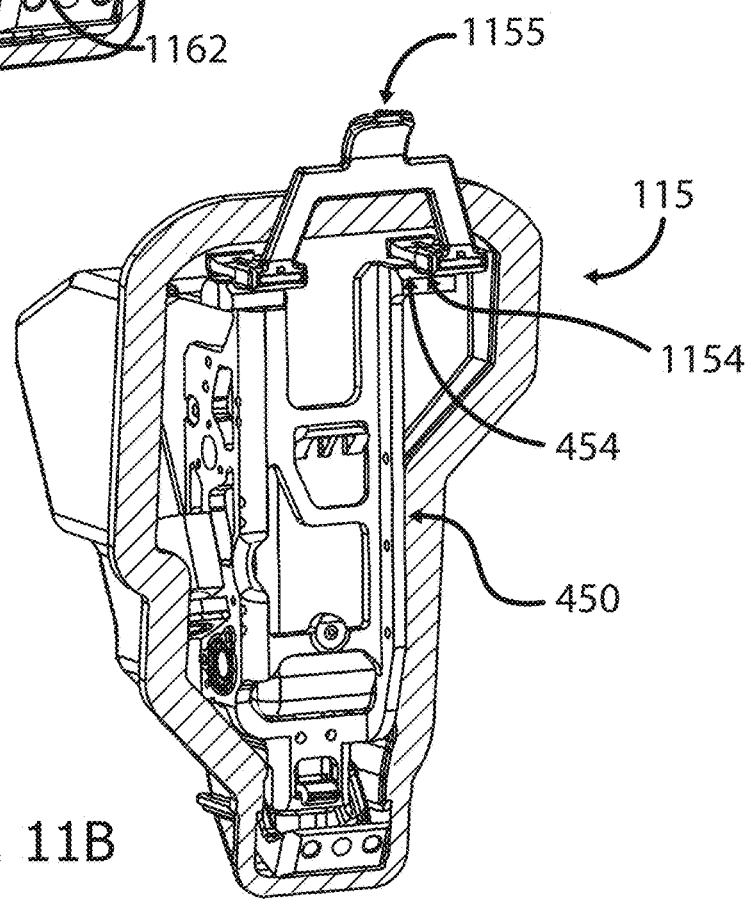

FIGS. 11A-11B show perspective back views of exemplary end effectors and drape adaptors coupled thereto. FIG. 11A shows an adaptor 110 which has a single latch 1164 for establishing a snap-fit connection with a corresponding single connector 404 of the end effector 400. The latch 1164 may be coupled to a release handle 1105, which the user pulls to release the latch 1164 from the connector 404 and enable removal of the adaptor 110 from the end effector 400. FIG. 11A further shows a gripper 1162 of the adaptor 110 anchored onto a dedicated anchoring bar 402 of the end effector 400. Coupling of the adaptor 110 to the end effector 400 may be carried out by the user first placing the adaptor's gripper 1162 on the end effector's anchoring bar 402, and then pivoting the adaptor 110 about the bar axis until the latch 1164 is captured by the end effector's connectors 404.

Also shown are the adaptor's positioning members 1166, 1168 coupled to the corresponding end effector's positioning members 406, 408 respectively. In some implementations, the positioning members 1166, 1168 may be used to ensure correct placement of the adaptor 110 on the end effector 400 and to further ensure the stability of the adaptor 110 on the end effector 400 once coupled to each other. For example, positioning member 1166 may be configured as a shelf-like protrusion which is received within an opening 406 in the end effector's 400 housing, such that it maintains contact with the upper and side walls of the opening. This is to ensure that once coupled, the adaptor 110 cannot move upwards or sideways relative to the end effector 400. The gripper 1162 being anchored on the anchoring bar 402 ensures that the adaptor 110 cannot move downwards relative to the end effector 400.

FIG. 11B shows an adaptor 115 and an end effector 450 which are similar to the adaptor and end effector of FIG. 11A, except that the adaptor 115 shown in FIG. 11B has two latches 1154 which establish a snap-fit connection with two corresponding connectors 454 of the end effector 450. The two latches 1154 may be coupled to a single release handle 1155, which the user can pull to release the latches 1154 from the connectors 454 and enable removal of the adaptor 115 from the end effector 450. Alternatively, each latch 1154 may be provided with its own separate release handle. It can be appreciated that the adaptor may include more than two latches and the end effector may include more than two connectors.

In the implementations, once the drape adaptor is coupled to the end effector, the user can couple the insertion module to the adaptor.

Figure 12A:
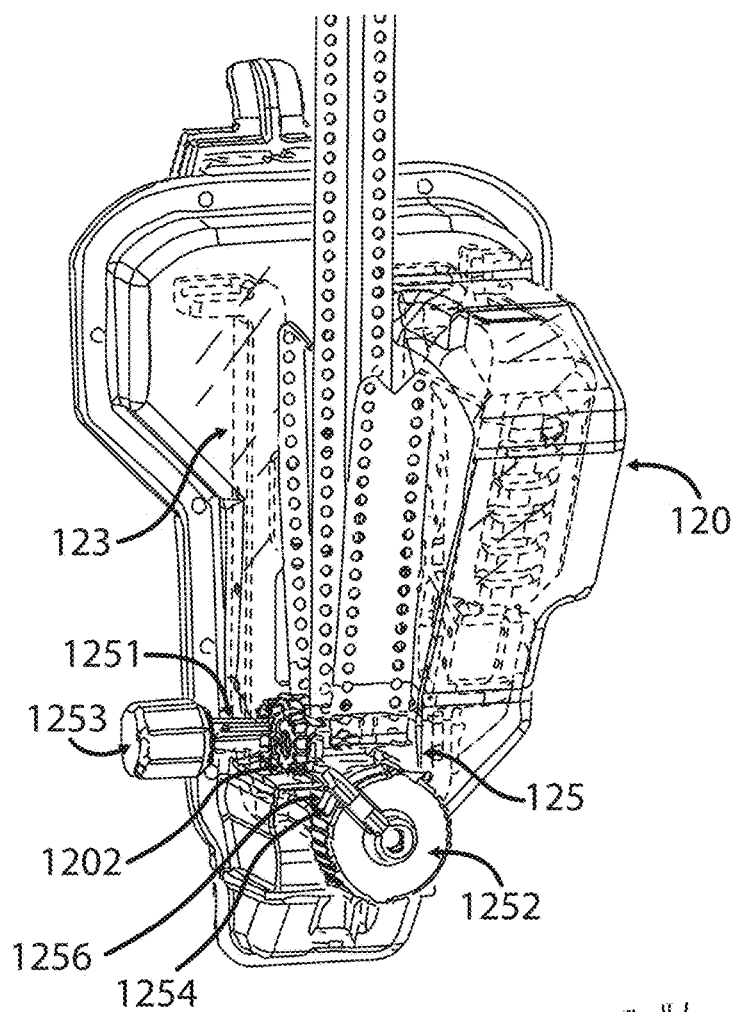
FIG. 12A shows a perspective view of the coupled end effector, drape adaptor and insertion module, according to implementations of the present disclosure.

FIG. 12A shows all three units, the end effector 123, the drape adaptor 120 and the insertion module 125, coupled to each other. In some implementations, the insertion module 125 is provided with its drive axis 1251 in the retracted state. Once the insertion module 125 is securely coupled to the adaptor 120 and end effector 123, the drive axis 1251 is transitioned from the retracted state to the extended state. The transition may occur automatically or manually, by the user pushing or rotating the activation knob 1253, depending on the specific implementation, which moves the drive axis 1251 to the extended state, until it is operatively coupled with the end effector 123. Operative coupling between the insertion module's drive axis 1251 and the end effector 123 enables activation of the insertion mechanism. Automatic transition between the retracted and extended states may occur, for example, via a mechanical trigger (not shown) which is activated (e.g., pressed) as the insertion module 125 reaches its desired position within the adaptor's receiving section 1202.

In some implementations, after the insertion module 125 is inserted into the adaptor's receiving section 1202, the user must rotate the insertion module's tightening knob 1252 to further push the insertion module 1252 into its final position within the adaptor's receiving portion 1202 and ensure proper coupling between the insertion module 1252 and the adaptor 120. As the tightening knob 1252 is rotated, capturing elements of the tightening knob 1252 engage with capturing members of the adaptor 120. It can be appreciated that the tightening knob may alternatively be activated via pressing of the knob.

Figure 12B:
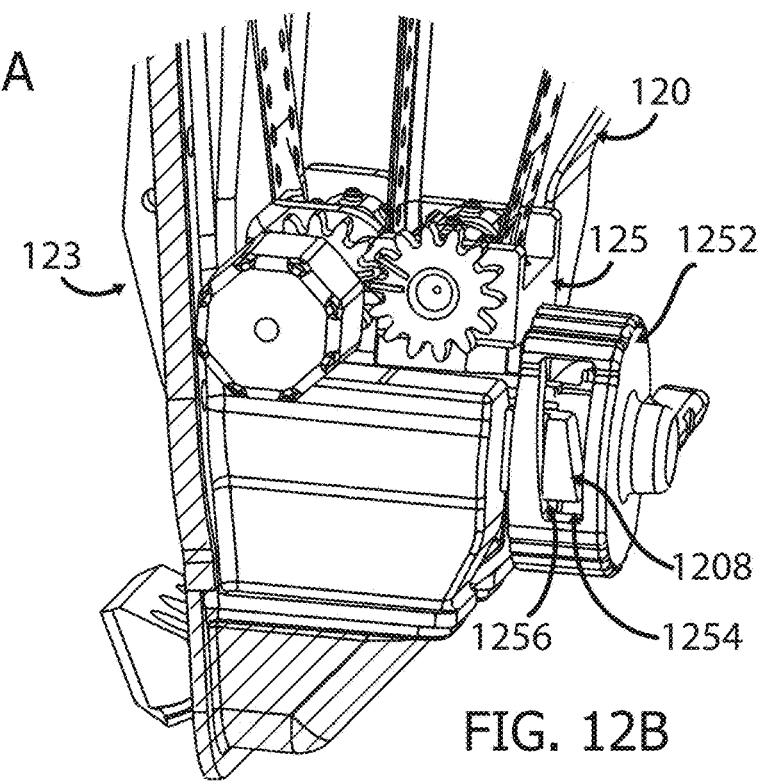
FIG. 12B shows the mechanism of tightening the insertion module to the drape adaptor using the insertion module's tightening knob, according to implementations of the present disclosure.

As shown in FIG. 12B, the capturing elements of the tightening knob 1252 may be slots 1254 on the circumference of the tightening knob 1252, which may have at least one inclined surface 1256, and the adaptor's capturing members may be stationary hook/s 1208. Since the surface 1256 is inclined in the direction of rotation, and the hook 1208 is stationary, then once contact is established between the inclined surface 1256 and the inner surface of the hook 1208, continued rotation of the tightening knob 1252 causes the inclined surface 1256 to be pushed inwardly (i.e., toward the adaptor's receiving section 1202) by the stationary hook/s 1208, resulting in linear movement of the tightening knob 1252, and thus of the entire insertion module 125 to which the knob 1252 is rigidly coupled, further into the adaptor's receiving portion 1202, until the insertion module 125 reaches its final position within the adaptor's receiving portion 1202, and the tightening knob 1252 cannot be rotated any further in the same direction.

Figure 13A:
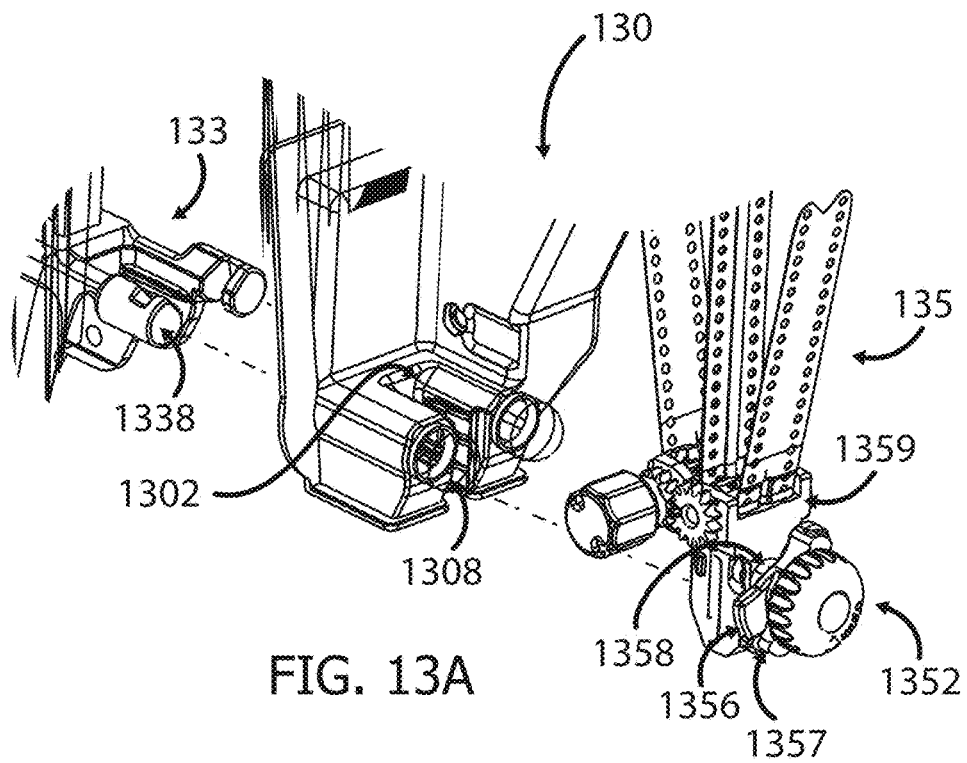
FIGS. 13A-13C show an alternative mechanism of tightening the insertion module to the drape adaptor, according to implementations of the present disclosure.
Figure 13B:
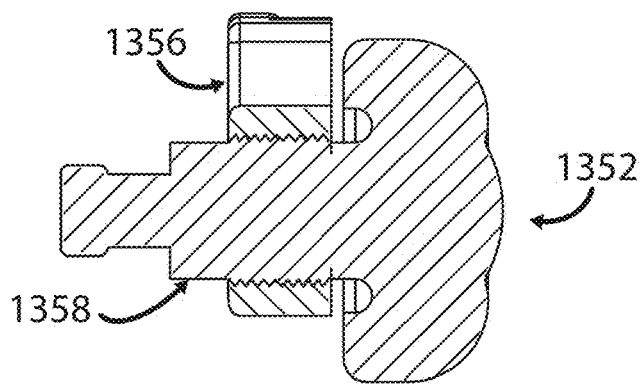
Figure 13C:
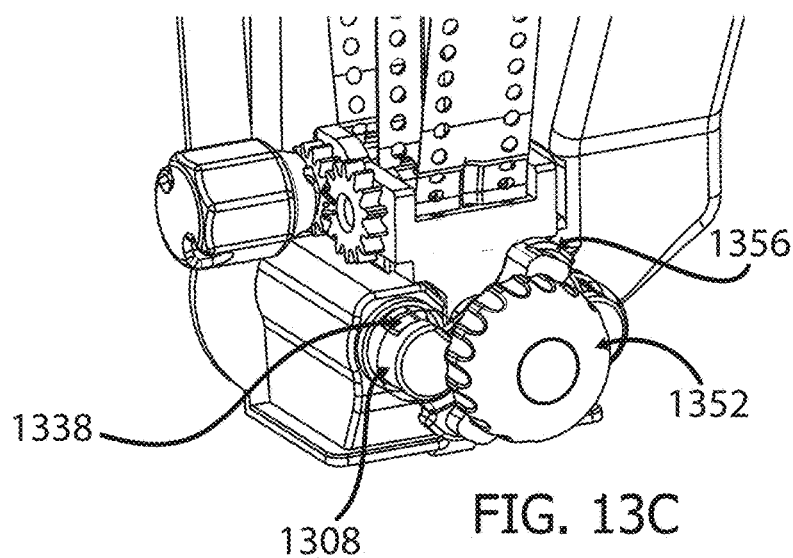

In an alternative implementation, shown in FIGS. 13A-13C, the stationary hooks 1338 may be part of the end effector 133.

FIG. 13A shows an exploded view of the end effector 133, insertion module 135 and drape adaptor 130. In some implementations, upon coupling the adaptor 130 to the end effector 133, hooks 1338 pass through dedicated openings 1308 in the adaptor 130, enabling the hooks 1338 to engage with the insertion module's tightening knob 1352 once the insertion module 135 is coupled to the adaptor 130. To prevent direct contact between the hooks 1338, which in such implementations are non-sterile being part of the end effector 133, and the sterile tightening knob 1352, the adaptor 130 may include elastic domes 1308 which cover the hooks 1338 while maintaining their functionality.

The capturing elements of the tightening knob 1352 may be configured as shown in FIGS. 12A-12B, or they may be configured as one or more external flags 1356 which engage with the hooks 1338 as the tightening knob 1352 is rotated. In some implementations, the tightening knob 1352 and the flags 1356 may be separate elements coupled via a threaded engagement, as shown in FIG. 13B. The flags 1356 may have gradually increasing thickness, such that upon coupling of the insertion module 135 to the adaptor 130, there is minimal or no contact between the flags 1356 and the hooks 1338, and therefore, when the user begins rotating the tightening knob 1352, the flags 1356 rotate together with the tightening knob 1352. As the flags 1356 rotate, a thicker and thicker portion of the flags 1356 passes by the hooks 1338, until the flags 1356 are positioned against the inner surface of the hooks 1338 (or—against the elastic domes 1308 covering the hooks 1338), such that the hooks 1338 prevent the continued rotation of the flags 1356. Continued rotation of the flags 1356 may alternatively (or in addition) be prevented by means of a step 1357 formed in the flags, which encounters a side (or top) surface of the hooks 1338 during rotation. As the user continues to rotate the tightening knob 1352, the flags 1356, which are now held in place by the hooks 1338, effectively serve as a nut for the shaft 1358 of the tightening knob 1352, which is at least partially threaded, and thus continued rotation of the tightening knob 1352 results in linear movement of the tightening knob 1352. The shaft 1358 then presses the insertion module housing 1359, and thus the entire insertion module 135, against the back end of the adaptor's receiving portion 1302, until the insertion module 135 reaches its final position within the adaptor's receiving portion 1302, and the tightening knob 1352 cannot be rotated any further.

In other implementations, the tightening knob 1352 and the flag/s 1356 may be formed as a single unit, such that linear movement of the tightening knob 1352, including the integral flags 1356, is enabled only as long as the flags 1356 can continue to rotate, i.e., until the hooks 1338 prevent continued rotation of the flags 1356.

FIG. 13C shows the end effector 133, insertion module 135 and drape adaptor 130 after coupling.

It can be appreciated that any other suitable mechanism may be used instead of the mechanisms described hereinabove in order to ensure proper coupling between the insertion module 135, adaptor 130 and end effector 133.

Figure 14A:
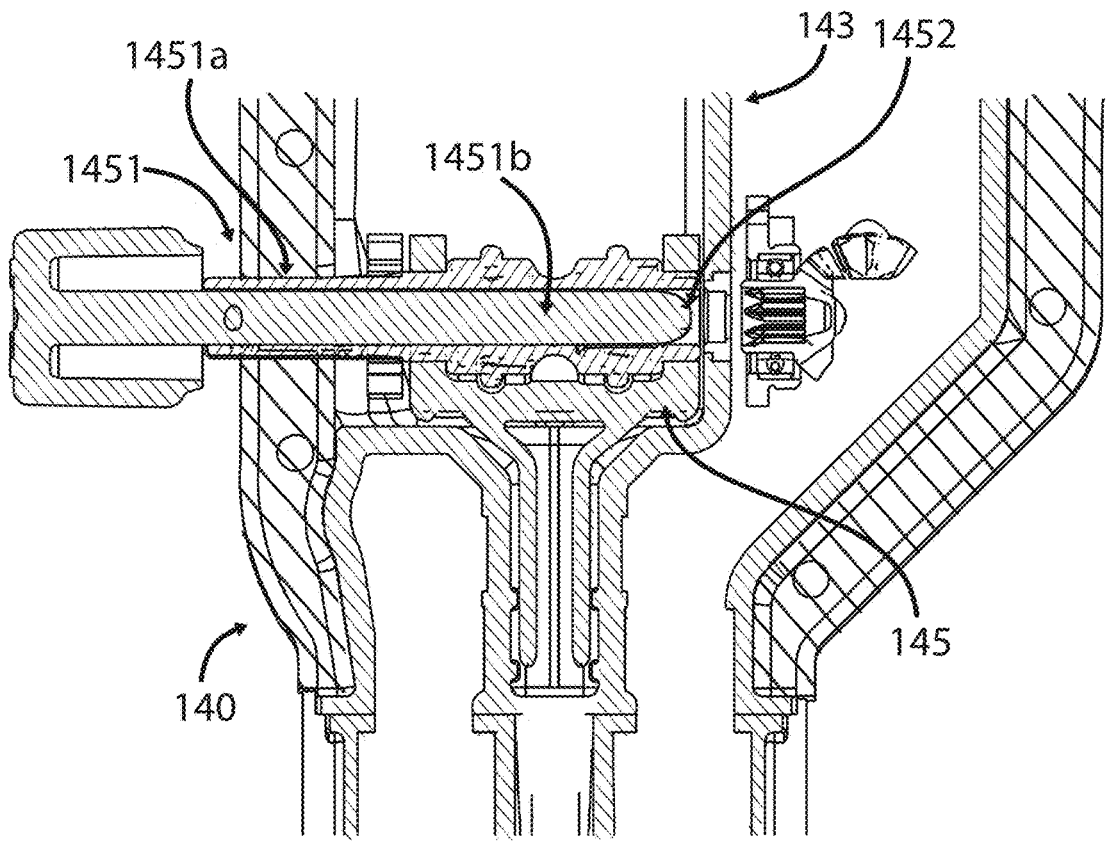
FIGS. 14A-14B show cross-sectional views of the coupled end effector, drape adaptor and insertion module, with the insertion module's drive axis in retracted (FIG. 14A) and extended (FIG. 14B) states, according to implementations of the present disclosure.
Figure 14B:
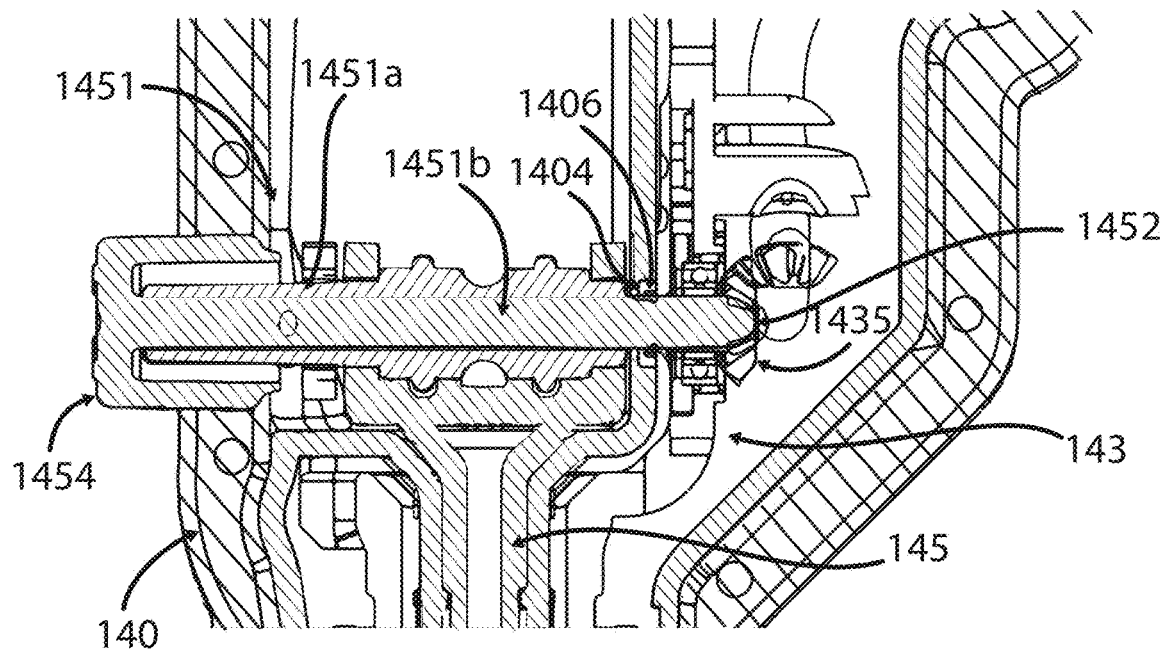

FIGS. 14A-14B show cross-sectional views of the coupled end effector 143, adaptor 140 and insertion module 145, with the insertion module's drive axis 1451 in retracted (FIG. 14A) and extended (FIG. 14B) states. As previously mentioned, the insertion module 145 may be provided with its drive axis 1451 in the retracted state, as shown in FIG. 14A. In the retracted state, the drive axis' inner part 1451b is positioned within the drive axis' outer part 1451a such that the inner part's tip 1452 is within the outer part 1451a as well, and does not extend beyond the insertion module's housing. Once the insertion module 145 is securely coupled to the adaptor 140, e.g., after rotation of the tightening knob (not shown in FIGS. 14A-14B), the drive axis 1451 is moved, either automatically or manually by the user, from the retracted state to the extended state, as shown in FIG. 14B, by movement of the drive axis' inner part 1451b within the outer part 1451a, until the inner part's tip 1452 is received within the female bevel gear 1435 of the end effector 143, rendering the insertion mechanism functional.

The drive axis' knob 1454 may be rigidly coupled to the drive axis' inner part 1451b, such that as the drive axis' inner part 1451b moves within the drive axis' outer part 1541a, the knob 1454 moves externally along the outer part 1451a and covers a portion of it.

Prior to being received within the female bevel gear 1435, the drive axis' tip 1452 passes through the opening 1404 of the adaptor 140, which is provided with a sealing member 1406, such as an O-ring. As the tip 1452 traverses the sealing member 1406, the sealing member 1406 surrounds the drive axis' inner part 1451b, thereby preventing leakage of contaminants through the opening 1404 into the sterile environment.

FIGS. 15A-15C show a modular insertion module 155 having two parts; a rear part 155a and a front part 155b. In some cases, once the needle has reached its target inside the patient's body, the user (e.g., physician) may prefer to leave only the needle in place and disconnect it from the insertion device, since the insertion device may obstruct his/her view or actions. In case the insertion device is body-mounted, the physician/clinician may wish to remove it from the patient's body altogether, while leaving only the needle itself inside the patient's body. The two-part configuration of the insertion module 155 allows the user to disconnect the two parts of the insertion module 155 from each other and remove them from the needle, such that the needle remains inserted within the patient's body, as disclosed in abovementioned U.S. Patent Application Publication No. 2017/0258489 and in abovementioned International Patent Application Publication No. WO/2018/055621. It can be appreciated that the modular insertion module 155 may include more than two parts.

FIG. 15A shows a bottom view of the two-part insertion module 155. In some implementations, each of the two parts 155a, 155b may include a portion of the insertion mechanism. The rear part 155a may include one flexible strip 1551a, the drive axis 1552, one gear 1553a and the drive roller (not shown in FIG. 15A), and the front part 155b may include the second flexible strip (not shown in FIG. 15A), gear 1553a, the driven roller (not shown in FIG. 15A) and the tightening knob 1554. The rear part 155a may further include the niche 1555, which may be used for either alignment/positioning of the insertion module 155 relative to the adaptor (not shown in FIG. 15A) or for rigid coupling of the rear part 155a to the adaptor. The connection between the rear and front parts 155a, 155b may be such that the two parts can be disconnected from each other by the user. For example, the connection between the two parts 155a, 155b may be a snap-fit connection, using connecting arms 1556 of the rear part 155a which are captured by side walls 1557 (or any other protruding element) of the front part 155b. It can be appreciated that the connecting arms may alternatively be part of the front part 155b and the side walls part of the rear part 155a.

FIG. 15B shows a transverse cross-sectional view of the coupled end effector 153, adaptor 150 and insertion module 155. In some implementations, the rigid connection between the rear part 155a of the insertion module 155 is established by means of a snap-fit connection. The insertion module's rear part 155a may have one or more protrusions 1558 which are captured by one or more protrusions 1504 located in the adaptor's receiving section 1502, such that once the snap-fit connection is established, the rear part 155a can no longer be disconnected from the adaptor 150. It can further be appreciated that the connection between the rear part 155a and the adaptor 150 should be stronger than the connection between the insertion module's rear and front parts 155a, 155b, so that any attempt to disconnect the front part 155b from the rear part 155a, while the insertion module 155 is coupled to the adaptor, would result only in the disconnection of the front part 155b from the rear part 155a, and thus from the adaptor, and not in undesired disconnection of the entire insertion module 155 from the adaptor.

Such implementations facilitate the disconnection of the two parts of the insertion module and minimize the number of parts to be handled and disposed of after use, as the insertion module's rear part is disposed of together with the adaptor, as a single unit.

FIG. 15C shows the end effector 153, adaptor 150 and insertion module 155 after disconnection of the insertion module's front part 155b from the insertion module's rear part 155a, which remains connected to the adaptor 150. Since the needle (not shown in FIG. 15C) is enclosed within the channel formed by the grooves 1559a, 1559b running along the strips' 1551a, 1551b longitudinal centerline, when the strips 1551a, 1551b are attached to each other, but it is not connected to the strips 1551a, 1551b, then once the needle has reached its target, the user can disconnect the two parts 155a, 155b from one another and away from the needle without applying on the needle any major forces which may cause it to move from its position. As previously mentioned, disconnection of the two parts 155a, 155b of the insertion module from each other, while the insertion module 155 is coupled to the adaptor 150, is possible when the connection between the two parts 155a, 155b is weaker than the connection between the insertion module's rear part 155a and the adaptor 150. A relatively weak snap-fit connection, for example, may enable disconnection of the two parts 155a, 155b by pulling of the front part 155b away from rear part 155a. The front part 155b is pulled until the two strips 1551a, 1551b, or more accurately—the top and unused portions of the strips, detach from one another and away from the needle. The user can then move the portion of the insertion device to which the end effector 153 is connected, such as a robotic arm (not shown), or the entire insertion device if the insertion device is body-mounted (not shown in FIG. 15C), away from the needle, leaving only the needle in its position inside the body. After decoupling the adaptor, together with the insertion module's rear part 155a rigidly coupled thereto, from the end effector 153, the disposable adaptor 150 and rear part 155a may be disposed of as one piece, and the insertion module's front part 155b may be disposed of separately.

Figure 16:
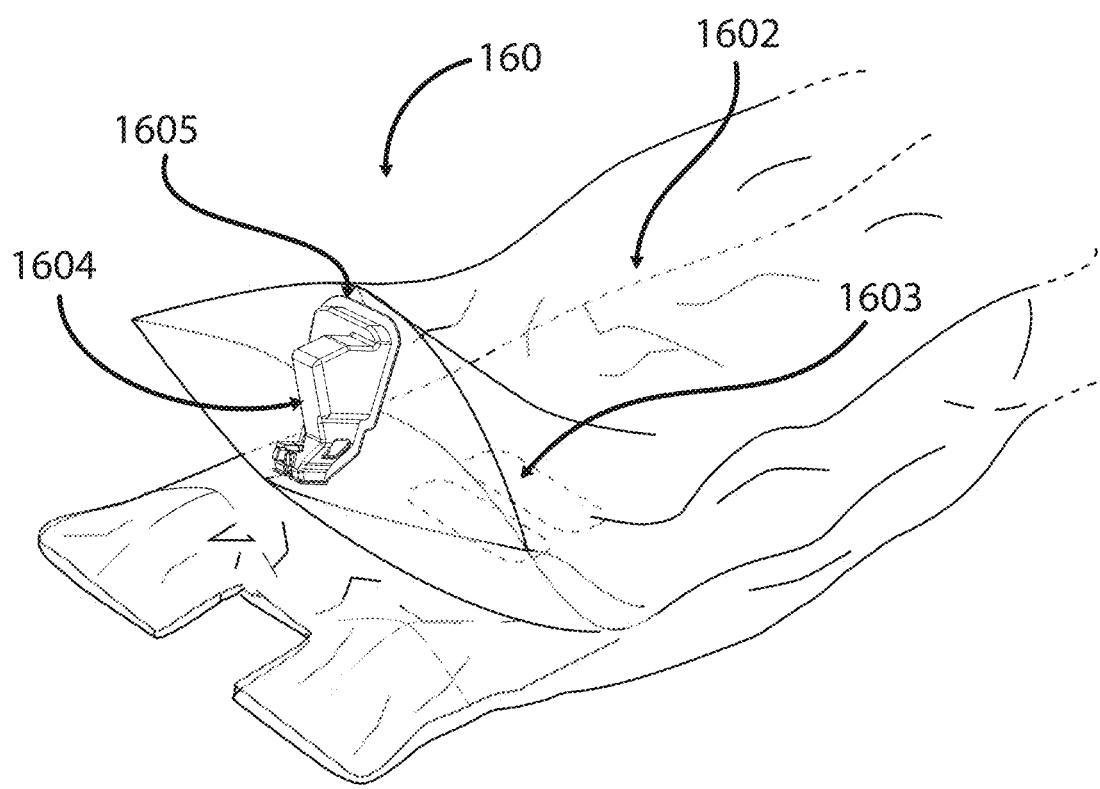
FIG. 16 shows a perspective view of an exemplary medical drape comprised of a drape sheet and a drape adaptor, according to implementations of the present disclosure.

FIG. 16 shows a perspective view of an exemplary medical drape 160 having a drape sheet 1602 and a drape adaptor 1604. The drape sheet 1602 may be fabricated from several separate sheets welded together to achieve a required drape design, or it may be a single sheet which is folded and welded within itself to reach the required drape design.

The drape sheet 1602 may be attached to the frame 1605 of the adaptor 1604 using heat welding, ultrasonic welding, ultraviolet (UV) curing or any other applicable attachment method. The medical drape 160 may be intended for use with a body-mounted medical device (not shown in FIG. 16), such that the drape adaptor 1604 is coupled to the medical device's end effector (not shown in FIG. 16) and the drape sheet 1602 covers the entire medical device, with its bottom portion placed on the patient's body and/or on a mediator base/plate positioned on the patient's body, either directly or on top of a standard drape sheet, which is used to prevent contact between non-sterile attachment members, such as straps (not shown in FIG. 16), and the patient's body.

In some implementations, the drape sheet 1602 may include one or more cushions/pads 1603 on its bottom surface, for patient comfort and/or for establishing friction between the drape sheet 1602 and the patient's body or the additional drape sheet, thus preventing relative movement/sliding.

Figure 17:
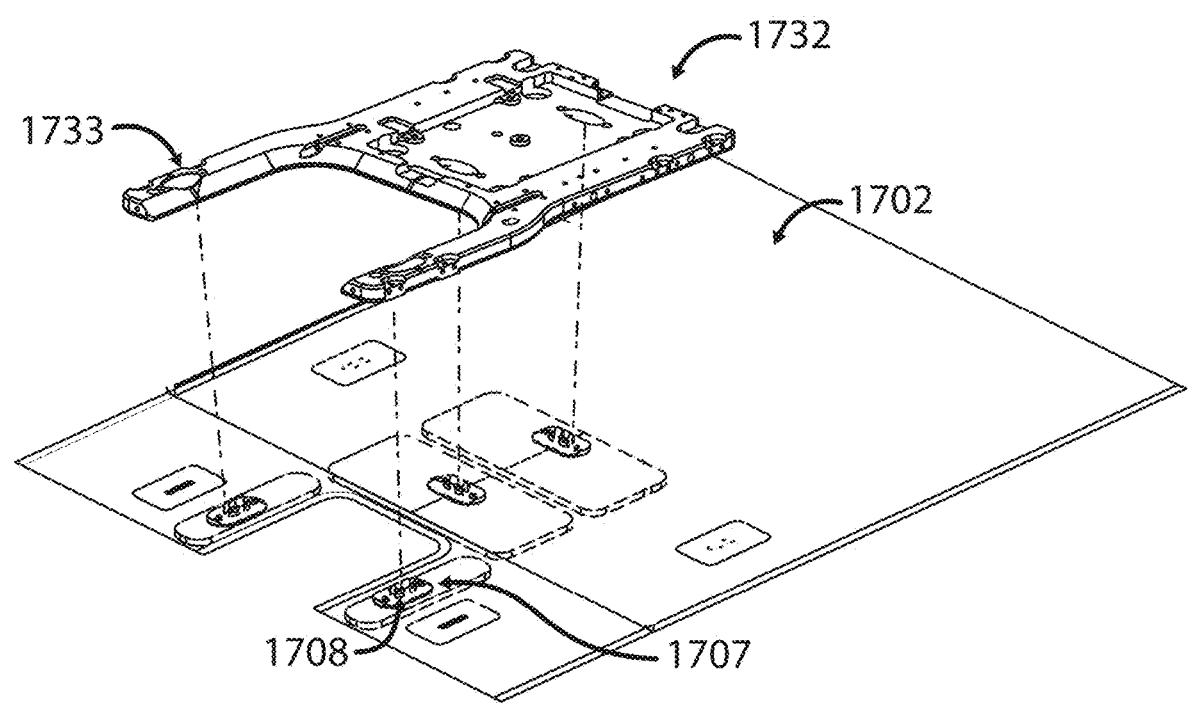
FIG. 17 shows a fastening mechanism for securing the drape sheet to the medical device's base, according to implementations of the present disclosure.

In some implementations, as shown in FIG. 17, the drape sheet 1702 may further include one or more fasteners 1707, to secure the drape sheet 1702 to the medical device, e.g., to the device's base 1732, after covering the medical device with the drape sheet 1702. The fasteners 1707 may each include one or more semi-flexible protrusions 1708, which fit within receiving holes 1733 in the device's base 1732, for example, such that pressing the fasteners 1707 against the holes 1733 causes the semi-flexible protrusions 1708 to latch on to the circumference of the holes 1733, and thus attach the drape sheet 1702 to the medical device's base 1732. The holes 1733 may be round, oval, rectangular or have any other shape and size. It can be appreciated that the drape sheet 1702 may be secured to the medical device's base 1732 using any other suitable securing means. Further, the drape sheet 1702 may be secured to a different part of the device, such as to the device's housing/cover (not shown in FIG. 17), instead of or in addition to its securing to the device's base 1732.

Figure 18A:
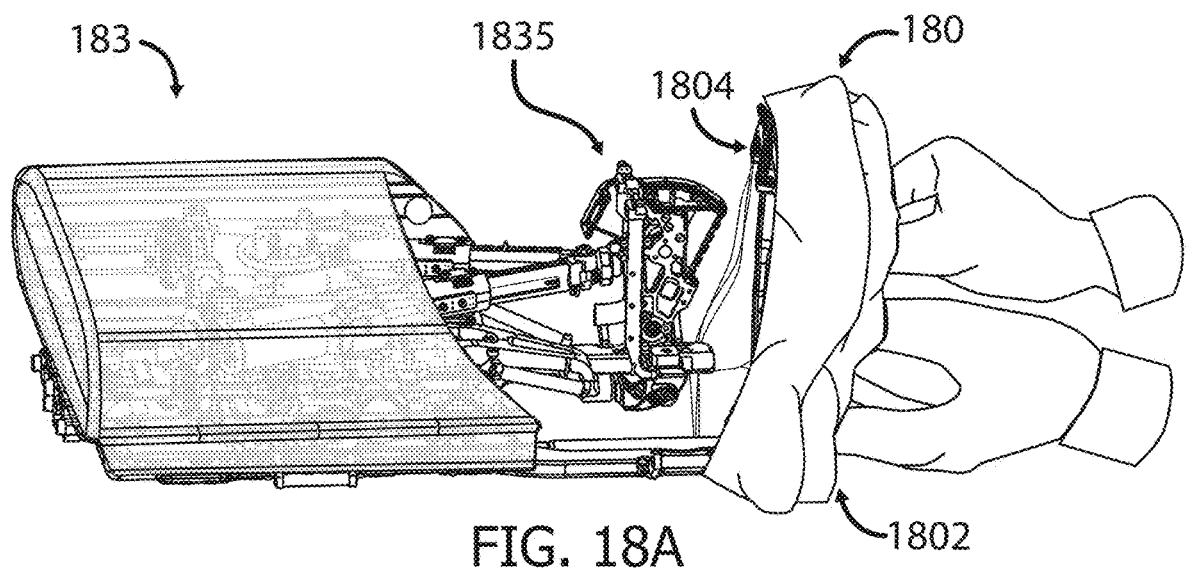
FIGS. 18A-18C show several stages of draping a medical device using the medical drape of FIG. 16, according to implementations of the present disclosure.
Figure 18B:
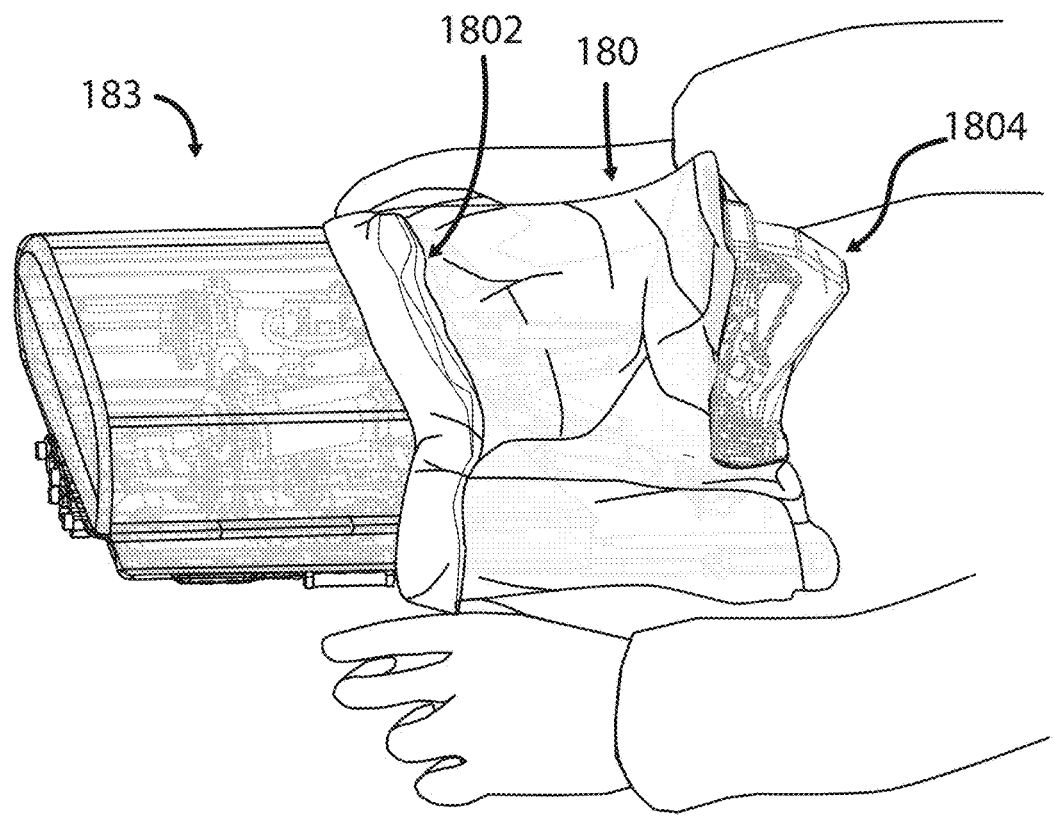
Figure 18C:
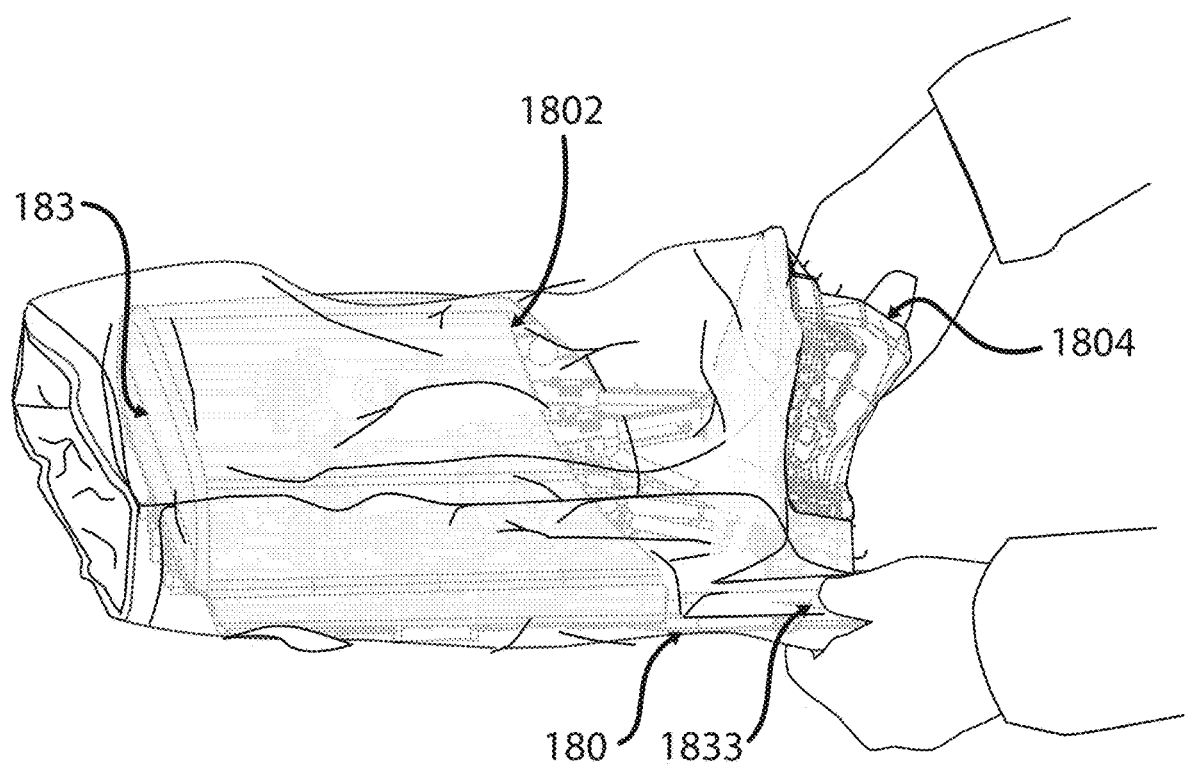

FIGS. 18A-18C show several stages of a user covering the automated medical device 183 using the medical drape 180 of FIGS. 16 and 17. If the medical device 183 is reusable and cannot undergo sterilization between procedures, since at least one of its components (e.g., electronic component) cannot undergo sterilization, for example, then prior to commencing the medical procedure the medical device 183 must be sufficiently covered, such that it will not come in contact with the patient and/or any person or sterile instrument which comes in contact with the patient during the medical procedure.

FIG. 18A shows the user holding the drape 180 close to the medical device 183, and preparing to couple the drape adaptor 1804 to the device's end effector 1835. At this stage, the drape sheet 1802 is folded back such that its external side, which must remain sterile, does not touch the medical device 183. FIG. 18B shows the user unfolding the drape sheet 1802 over the medical device 183 so as to cover the device 183, after the drape adaptor 1804 has been coupled to the end effector 1835. FIG. 18C shows the medical device 183 completely covered by the drape 180, and the user securing the drape sheet 1802 to the device 183, by pressing the fastener/s (not shown in FIG. 18C) against the device's receiving hole/s 1833. In some implementations, the medical device may be coupled to the device controller, its work station, etc., by means of a plurality of electrical cables extending from the rear of the device. In such implementations, once the device is completely covered by the drape 180, the user may close and secure the open end of the drape sheet 1802 around the cables, e.g., using an adhesive tape.

Figure 19:
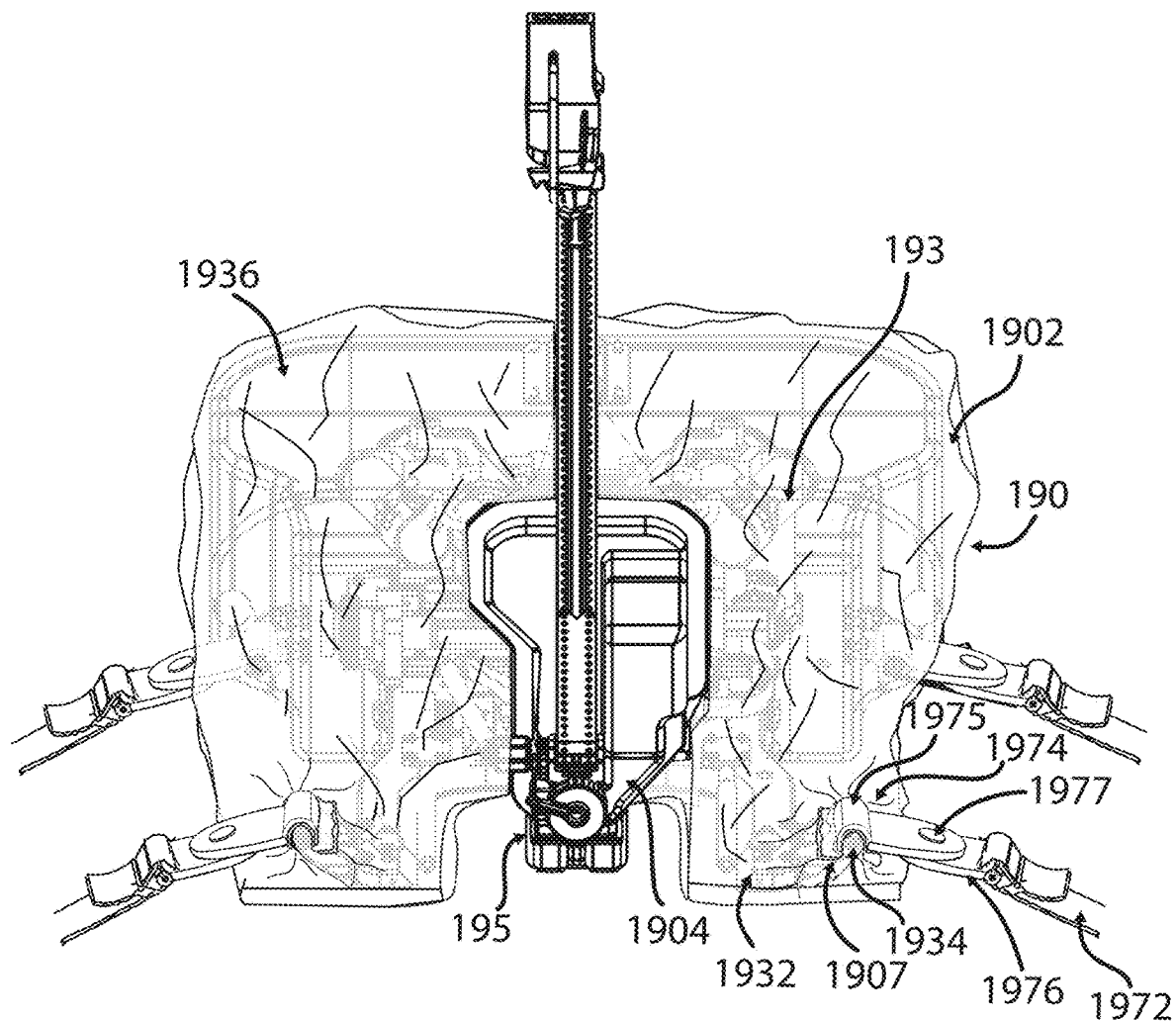
FIG. 19 shows the draped medical device attached to the patient's body, and the insertion module coupled thereto, according to implementations of the present disclosure.

FIG. 19 shows a draped medical device 193 attached to the patient's body, with the insertion module 195 coupled to the drape adaptor 1904. In some implementations, the insertion module 195 is coupled to the adaptor 1904 only after attaching the device 193 to the patient's body 5, whereas in other implementations, the insertion module 195 is coupled first to the adaptor 1904 and the device 193 is then attached to the patient's body. In further implementations, the insertion module 195 and the drape adaptor 1904, and therefore, the entire drape 190, as the adaptor 1904 is rigidly connected to the drape sheet 1902, are a single integral disposable unit.

The attachment of the medical device 193 to the patient's body may be done using any suitable attachment mechanism, for example, using one of the mechanisms disclosed in abovementioned International Patent Application Publication No. WO 2017/179044.

In some implementations, the medical device's base 1932 may comprise one or more anchors 1934, to which attachment straps 1972 are secured. The anchors 1934 may be positioned such that the connection of the straps 1972 to the base 1932 takes place higher than skin level, in order to produce larger perpendicular forces and thus provide a more durable and stable attachment of the medical device 193 to the body. It can be appreciated that the anchor/s 1934 may otherwise be attached to a different component of the device 193, such as to the device's housing/cover 1936. The straps 1972 may be provided with strap connectors 1974, which may comprise hook members 1975 adapted to latch on to the anchors 1934 of the medical device 193, over the drape sheet 1902. It can be appreciated that the drape sheet 1902 may be manufactured, at least at the sections over which the hook members 1975 latch on to the anchors 1934, from a resilient material, so as to prevent ripping as the hook members 1975 latch on to the anchors 1934, and/or that the sections of the drape sheet 1902 over which the hooks 1975 latch on to the anchors 1934 may be reinforced, e.g. they may have a double sheet layer or patches 1907 attached thereon. Using such patches 1907 and/or double sheet layers may also assist the user while he/she is covering the medical device 193 by serving as guides for properly positioning the drape sheet 1902 relative to the medical device 193, as the patches 1907 and/or double sheet layers are to be positioned directly over the anchors 1934. In some implementations, the hooks 1975 may be manufactured from such a material that will minimize the risk of ripping the drape sheet 1902 as the hooks 1975 are latched on to the anchors 1934, and/or the hooks 1975 may be coated, at least partially, with a resilient material, such as rubber, sponge, etc. In some implementations, the hook members 1975 may have rounded corners.

In some implementations, the straps 1972 may be attached directly to the hooks 1975. In other implementations, the strap connectors 1974 may further include rotating members 1976, which are attached to the straps 1972 at one end and to the hooks 1975, e.g., via a hinge 1977, at the opposite end, to allow adjustment of the strap's position and orientation on the patient's body via pivoting of the rotating member 1976, after the hook member 1975 has been coupled to the anchor 1934.

Figure 20A:
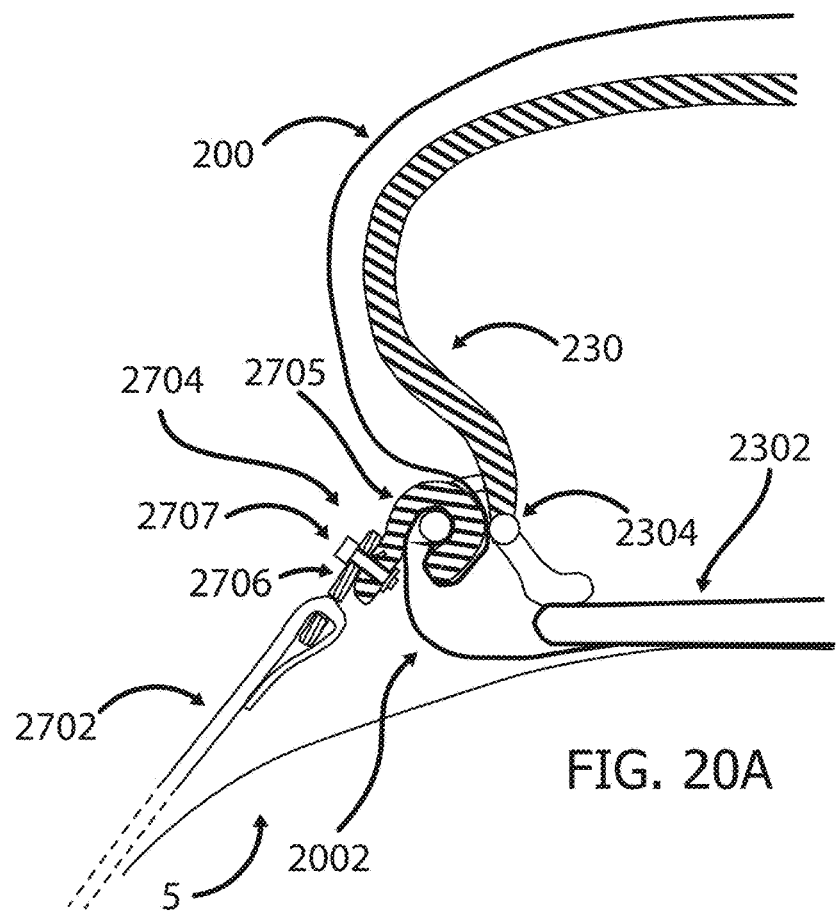
FIGS. 20A and 20B show cross-sectional views of a schematic medical devices covered by a drape and attached to the patient's body using at least one strap, according to implementations of the present disclosure.

FIG. 20A shows a cross-sectional view of a schematic medical device 230 covered by a drape 200 and attached to the patient's body using at least one strap 2702. The strap 2702 is connected to the device 230 using a strap connector 2704, which may include a hook member 2705 that can latch on to the anchor 2304 of the device's base 2302, over the drape sheet 2002, such that the sterile environment remains intact. The strap connector 2704 may further include a rotating member 2706, coupled to the hook 2705 via a hinge 2707, for example, such that the strap 2702 is not coupled to the hook member 2705 but to the rotating member 2706, allowing the user to adjust the strap's position and orientation on the patient's body 5, as needed. In some implementations, the bottom surface of the drape sheet 2002 may be provided with a low adherence glue (not shown) for attaching the draped device to the patient's body 5, or to a mediator base/plate (not shown) positioned on the patient's body to which the device may be coupled, such that the straps 2702 are complementary to the adhesive to ensure a durable attachment.

In some implementations, the hook member 2705 may be passed through an opening (not shown) in the drape sheet 2002, and in order to maintain a sterile environment, the drape sheet 2002 may be re-sealed by welding or adhering it around the hook member 2705.

Figure 20B:
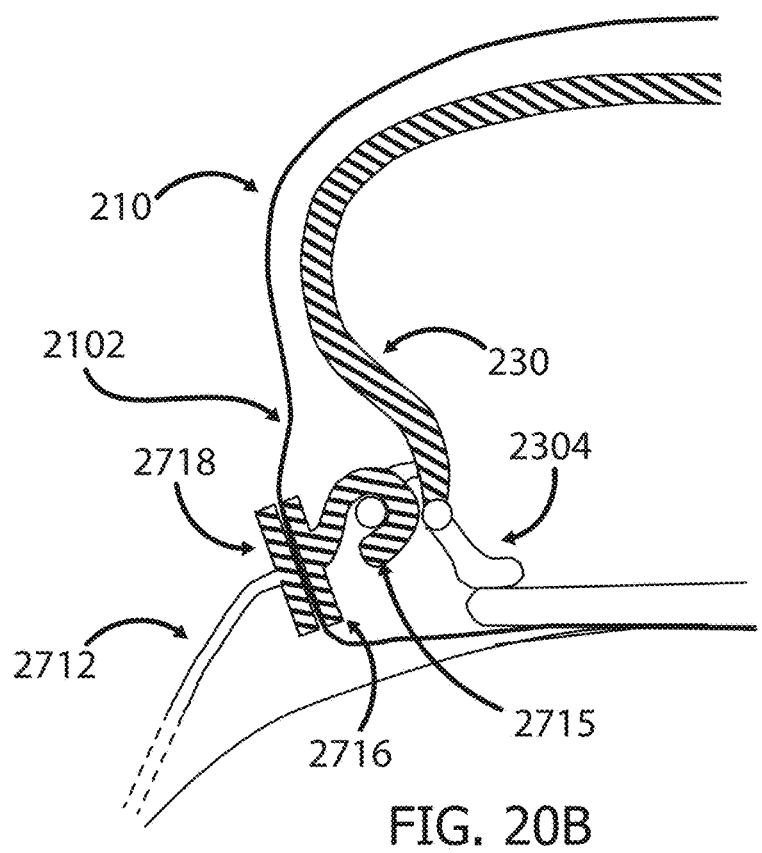

FIG. 20B shows a cross-sectional view of a schematic medical device 230 covered by a drape 200 and attached to the patient's body using at least one strap 2702, which is attached to the external (sterile) side of the drape sheet 2102, while the hook member/s 2715 is attached to the inner (non-sterile) side of the drape sheet 2102. Such an implementation minimizes the risk of the drape sheet 2102 being torn by the hook members 2715, which may compromise the sterile environment. The attachment of the hooks 2715 and the straps 2702 to the drape sheet 2102 may be carried out using an adhesive, ultrasonic welding, etc., and the attachment location may be determined such that the straps 2702 and the hook members 2715 are positioned at the same location, on opposite sides of the drape sheet 2102. In some implementations, the hook members 2715 and the straps 2702 may be provided with dedicated bases 2716, 2718 respectively, for attachment to the drape sheet 2102.

Figure 21A:
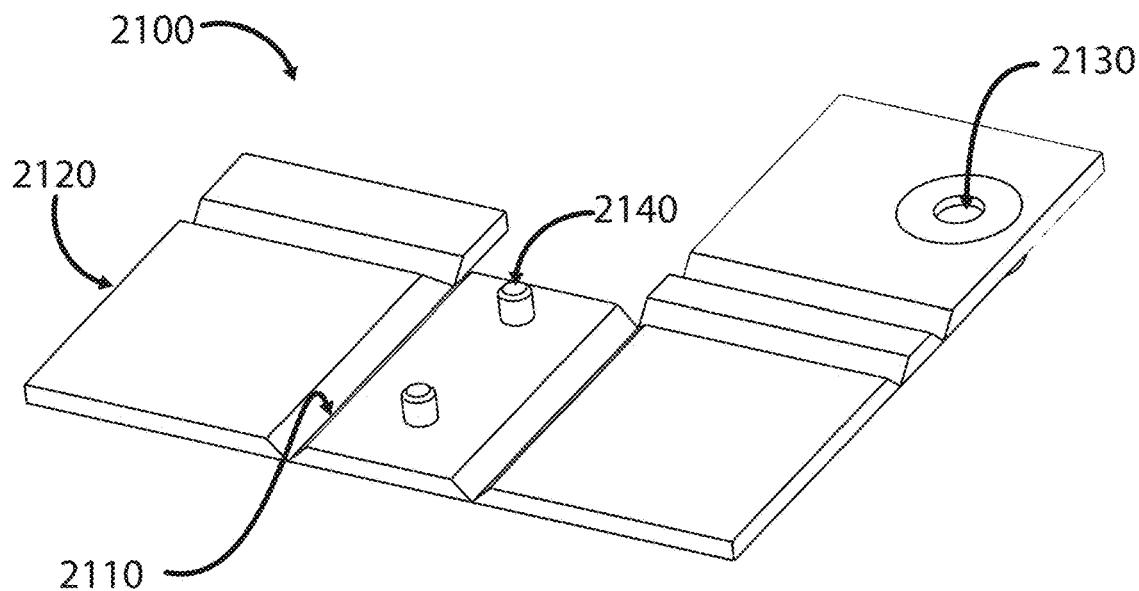
FIGS. 21A and 21B show an exemplary foldable drape adaptor, according to implementations of the present disclosure.
Figure 21B:
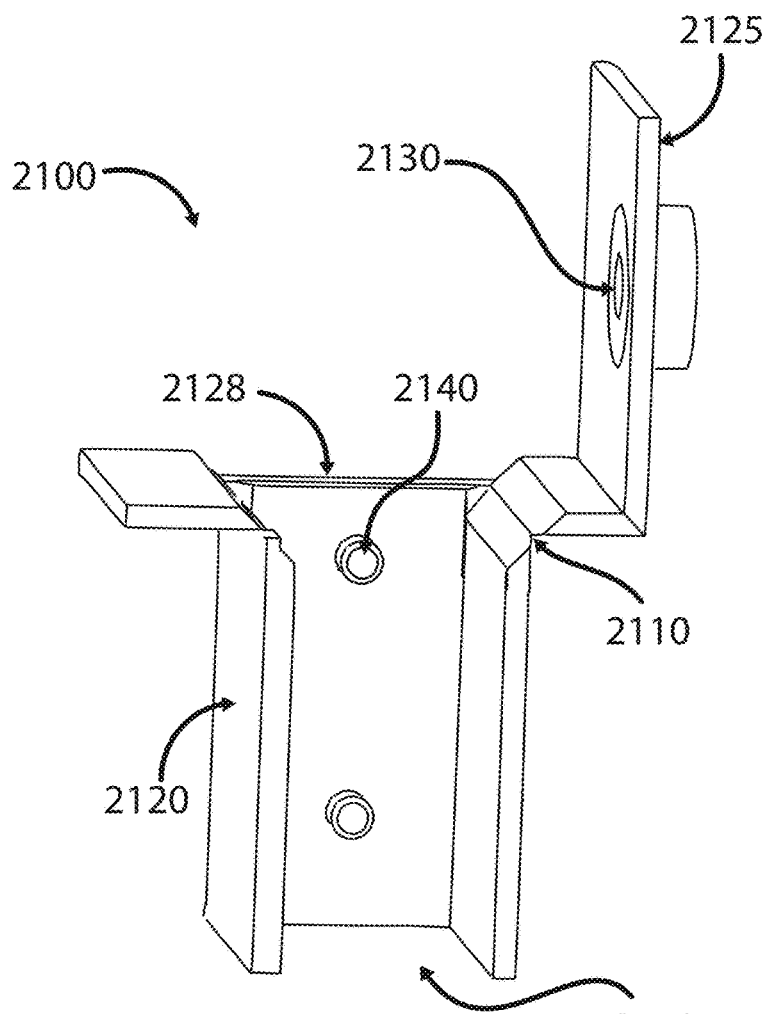

FIGS. 21A and 21B show an exemplary foldable drape adaptor 2100. FIG. 21A shows the foldable drape adaptor 2100 in its flat state, prior to being folded. In some implementations, using a foldable drape adaptor 2100 may facilitate attachment of the drape sheet (not shown in FIGS. 21A and 21B) to the adaptor 2100, as the attachment can be carried out, such as by means of heat welding or ultrasonic welding, while the adaptor 2100 is in its flat two-dimensional state, prior to folding it to its folded state. Attaching the drape sheet to a two-dimensional adaptor may be easier than attaching the drape sheet to a three-dimensional adaptor, in terms of manufacturability. Further, when the drape sheet is attached to a two-dimensional adaptor rather than to a three-dimensional adaptor, it may be easier to ensure that the sealing is not breached at the attachment lines/points.

The foldable adaptor 2100 may include a plurality of integral hinges 2110, which may be integral hinge lines, formed by narrowing of the thickness of the adaptor walls 2120, such that the adaptor 2100 is folded into its predefined shape along the integral hinges 2110. In some implementations, the adaptor 2100 may include an opening 2130, similar to opening 912 of FIG. 9A, for allowing passage of the drive axis of the insertion module (not shown in FIG. 21A) therethrough. The opening 2130 may be provided with a sealing member (not shown in FIG. 21A), such as an O-ring, overmold elastomeric material, etc., to prevent any possible leakage of contaminants through the opening 930 into the sterile environment. The foldable adaptor 2100 may further include one or more alignment members, such as protrusions 2140, which may fit within corresponding niches located in the back portion of the insertion module when the insertion module is coupled to the adaptor 2100. In some implementations, the alignment members 2140, together with the corresponding niches, may further provide rigid coupling between the adaptor 2100 and the insertion module, or at least the rear part of the insertion module, if a modular insertion module is utilized.

FIG. 21B shows the foldable drape adaptor 2100 in its folded state, after folding the adaptor walls 2120 along the integral hinge lines 2110. In the folded state, the opening 2130 is located in the wall 2125 which is intended to face the end effector (not shown in FIG. 21B), and the alignment members 2140 are located on back wall 2128 of the adaptor's receiving portion 2150, which is intended to receive the insertion module.

Although particular implementations have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the disclosure as defined by the claims. Other aspects, advantages, and modifications are considered to be within the scope of the following claims. The claims presented are representative of the implementations and features disclosed herein. Other unclaimed implementations and features are also contemplated. Accordingly, other implementations are within the scope of the following claims.

The invention claimed is:

1. A drape adaptor, comprising:
an adaptor body configured for coupling to a first component of a reusable unit of a medical device and for coupling a disposable unit of the medical device to the adaptor body, said disposable unit is configured for receiving an insertable medical tool, said first component comprising a non-sterile portion of a driving mechanism;
at least a portion of at least one component of a sterile portion of said driving mechanism; and
a sealing member positioned between the non-sterile portion of said driving mechanism and the sterile portion of said driving mechanism, wherein the sealing member is coupled to the adaptor body,
wherein said drape adaptor is configured to enable transmission of torque from said first component of said reusable unit of said medical device to said insertable medical tool via direct engagement between said at least one component of said sterile portion of said driving mechanism and said non-sterile portion of said driving mechanism, by translation through said sealing member, without compromising the sterility of the environment external to said drape adaptor,
wherein said adaptor body comprises a substantially rigid portion configured for covering at least a portion of said first component of said reusable unit of said medical device and a substantially elastic portion configured for covering at least a portion of a second component of said reusable unit of said medical device; and
further comprising one or more rear connectors configured to couple said adaptor body to said first component of said reusable unit of said medical device and one or more release handles coupled to said one or more rear connectors and configured to release said adaptor body from said first component of said reusable unit of said medical device.

2. The drape adaptor according to claim 1, wherein said adaptor body comprises a projecting section configured for covering at least a portion of said non-sterile portion of said driving mechanism.

3. The drape adaptor according to claim 1, wherein said adaptor body comprises an opening, and wherein said sealing member is disposed within said opening.

4. The drape adaptor according to claim 1, wherein said drape adaptor is configured to be foldable.

5. The drape adaptor according to claim 1, wherein said insertable medical tool comprises one or more of: a needle, an introducer, a catheter, a cannula, a port, an electrode rod, a surgical tool and a fluid delivery tool.

6. The drape adaptor according to claim 1, wherein the sealing member is configured for closing on said at least one component of said sterile portion upon said at least a portion of said at least one component passing through the sealing member.

* * * * *